(12) United States Patent
Frijns et al.

(10) Patent No.: US 11,598,765 B2
(45) Date of Patent: Mar. 7, 2023

(54) FLATBED AIR-LIQUID INTERFACE EXPOSURE MODULE AND METHODS

(71) Applicants: VITO NV, Mol (BE); Paris-Lodron-Universität Salzburg, Salzburg (AT)

(72) Inventors: Evelien Frijns, Mol (BE); Johan Van Laer, Mol (BE); Sandra Verstraelen, Mol (BE); An Jacobs, Mol (BE); Albert Duschl, Salzburg (AT); Martin Himly, Salzburg (AT); Pierre Madl, Salzburg (AT)

(73) Assignees: VITO NV, Mol (BE); Paris-Lodron-Universität Salzburg, Salzburg (AT)

( * ) Notice: Subject to any disclaimer, the term of this patent is extended or adjusted under 35 U.S.C. 154(b) by 805 days.

(21) Appl. No.: 16/463,447

(22) PCT Filed: Nov. 23, 2017

(86) PCT No.: PCT/EP2017/080241
§ 371 (c)(1),
(2) Date: May 23, 2019

(87) PCT Pub. No.: WO2018/096046
PCT Pub. Date: May 31, 2018

(65) Prior Publication Data
US 2019/0277832 A1 Sep. 12, 2019

(30) Foreign Application Priority Data

Nov. 24, 2016 (EP) .................................... 16200571

(51) Int. Cl.
*G01N 33/50* (2006.01)
*C12M 1/12* (2006.01)
(Continued)

(52) U.S. Cl.
CPC ......... *G01N 33/5014* (2013.01); *C12M 25/04* (2013.01); *C12M 35/02* (2013.01);
(Continued)

(58) Field of Classification Search
CPC ...... C12M 25/04; C12M 41/12; C12M 41/46; C12M 35/02; C12N 5/0688; C12N 13/00; G01N 33/5014
See application file for complete search history.

(56) References Cited

U.S. PATENT DOCUMENTS

2008/0047825 A1 * 2/2008 Petrucci ................. B82Y 15/00
422/186.04
2010/0151571 A1 * 6/2010 Vukasinovic .......... C12M 41/12
435/303.1
(Continued)

FOREIGN PATENT DOCUMENTS

WO     2010/040473 A2     4/2010
WO     WO-2010040473 A2 * 4/2010     ............ C12M 23/00

OTHER PUBLICATIONS

Anke Babriele Lenz et al. "A dose-controlled system for air-liquid interface cell exposure and application to zinc oxide nanoparticles." Particel and Fibre Toxicology. 2009, 6:32, pp. 1-17. (Year: 2009).*
(Continued)

*Primary Examiner* — Michael L Hobbs
(74) *Attorney, Agent, or Firm* — Banner & Witcott, Ltd.

(57) ABSTRACT

The present invention relates to a flatbed air-liquid interface exposure module for exposing a plurality of cells at an air-liquid interface to nanoparticles, the flatbed air-liquid interface exposure module comprising a moisturizing section, an exposure section, and an aerosol duct. Further provided are related systems and methods.

15 Claims, 13 Drawing Sheets

(51) Int. Cl.
  *C12M 1/34*     (2006.01)
  *C12M 1/42*     (2006.01)
  *C12N 13/00*    (2006.01)
  *C12N 5/071*    (2010.01)

(52) U.S. Cl.
  CPC ............ *C12M 41/12* (2013.01); *C12M 41/46* (2013.01); *C12N 5/0688* (2013.01); *C12N 13/00* (2013.01)

(56) References Cited

U.S. PATENT DOCUMENTS

2011/0212515 A1    9/2011   Mohr et al.
2013/0217113 A1*   8/2013   Srinivasan ............. C12N 13/00
                                                        435/306.1

OTHER PUBLICATIONS

Dec. 29, 2015—Stoehr, Linda C. Supplemental Material "Assessment of a panel of interleukin-8 reporter lung epithelial cell lines to monitor the pro-inflammatory response following zinc oxide nanoparticle exposure under different ell culture conditions" Particle and Fibre Toxicology, vol. 12, No. 1.

Dec. 29, 2015—Stoehr, Linda C. "Assessment of a panel of interieukin-8 reporter lung epithelial cell lines to monitor the pro-inflammatory response following zinc oxide nanoparticle exposure under different ell culture conditions" Particle and Fibre Toxicology, vol. 12, No. 1.

Dec. 16, 2009—Gabriele, Lenz Anke et al., "A dose-controlled system for air-liquid interface cell exposure and application to zinc oxide nanoparticles" Particle and Fibre Toxicology, Biomed Central, vol. 6 No. 1.

Feb. 12, 2018—PCT/EP2017/080241 ISR&WO.

* cited by examiner

A

B

FLATBED AIR-LIQUID INTERFACE EXPOSURE MODULE AND METHODS

CROSS-REFERENCE TO RELATED APPLICATIONS

This application is a U.S. National Stage application under 35 U. S. C. § 371 of International Application PCT/EP2017/080241 (published as WO 2018/096046 A1), filed Nov. 23, 2017, which claims the benefit of priority to Application EP 16200571.4, filed Nov. 24, 2016. Each of these prior applications is hereby incorporated by reference in its entirety.

FIELD OF THE INVENTION

The present invention relates to a testing system for mimicking the natural lung environment. Further provided are methods for determining the effect of nanoparticles on cells and methods for screening based on the effect of nanoparticles on cells.

BACKGROUND OF THE INVENTION

Many prior art methods for nanotoxicity testing suffer from significant disadvantages. For example in vitro-systems featuring submerged cultures involve nanoparticles and cells in a liquid, which does not correspond to the physiological environment of the lungs.

To overcome the deficiencies of submerged nanotoxicity testing, as reviewed by Paur et al. (J. Aerosol Sci. 2011, 42 668-692), several in vitro systems have been developed for exposure of cells at the air-liquid interface (ALI) to aerosolized nanoparticles (NPs), allowing a more realistic interaction between pulmonary cells and NPs, limiting alterations of the physicochemical properties of the NPs, and providing a more accurate dose determination. Most of the methods described in the literature are in-house systems, e.g. ALICE (Lenz et al. Part Fibre. Toxicol. 2009, 6 32) and ALIDA, but there are also commercially available systems like the CULTEX (Cultex Laboratories GmbH) and the VITROCELL® (VITROCELL systems GmbH) exposure technology with proven effectiveness.

Most ALI experiments are based on diffusion and/or gravitational settling as deposition mechanisms with a typically fairly low deposition (Aufderheide, M. Exp. Toxicol Pathol. 2008, 60 (2-3), 163-180; Bitterle et al. Chemosphere. 2006, 65 (10), 1784-1790; Diabate et al. 2008, 36 (3), 285-298; Rothen-Rutishauser et al. J. Environ Sci. Technol. 2009, 43 (7), 2634-2640, Steinritz et al. Chem Biol. Interact. 2013, 206 (3), 479-490).

Moreover, an air-liquid interface in which nanoparticles are deposited on lung cells by means of a mist, also does not correspond to the natural environment in the lungs. Still different systems involve the use of guided air flow, which unfortunately results in a straw stalk effect and nanoparticles rebounding on the air-liquid interface.

US2008/0047825 discloses a particle exposure system for exposing a target material to charged particles. The particle exposure system includes an exposure chamber with an upper wall, lower wall and one or more sidewalls that together define the exposure chamber for containing target material and receiving the particles during use. The exposure chamber includes a pedestal mounted to the lower wall of the exposure chamber, with a first electrode incorporated into an upper part of the pedestal. The first electrode may take the form of a plate, a mesh, coil etc. A generally flat layer of target material is disposed on the upper face of the electrode and is exposed to the exposure chamber. From a lower face of the electrode, protrusions may extend into the remainder of the material of the pedestal. The second electrode is spaced from the first electrode that extends from the upper wall. The exposure chamber contains in the lower wall one or more outlets for exhausting a gas or gas/particle mixture supplied to the chamber, in such a way that a gas stream directed at the center of the target material can readily flow over and to the sides of the target material and pedestal. The second electrode may be movable in a direction toward and away from the first electrode.

WO2010/040473 discloses a culture/exposure device for cell and/or bacteria cultures, comprising receptacles for individual cultural containers provided in a base body, a flow guide having an inlet aimed at exposing the cultural containers to a test atmosphere. The test atmosphere may be a gaseous medium, which carries particles, for example an aerosol The device comprises a plurality of modules which are connected to each other in such a manner that they are easily detachable from each other. The sample receptacle module is connected to an aerosol guiding module, on which there sits a preparatory module. The preparatory module can, for example, be formed as a charger, in which instance a test atmosphere is charged, for example, in an electrostatic manner. This module could be replaced by a moisturizer, in which the test atmosphere is moisturized, or by a simple inlet adapter, if no pretreatment of the test atmosphere is required.

Lenz Anke Gabriele et al disclose in Particle and fibre technology, Boimed Central London, GB, vol. 6, no. 1, 16 Dec. 2009, page 32 an air-liquid interface cell exposure system for nanoparticles in liquids. The device generates a dense cloud of droplets with a vibrating membrane nebulizer and utilizes combined cloud settling and single particle sedimentation for efficient delivery of nanoparticles at the air-liquid interface.

In view of the above, there is a clear need for in-vitro air-liquid interface exposure systems which closely mimic in-vivo exposure to nanoparticles.

SUMMARY OF THE INVENTION

The inventors have developed a flatbed air-liquid interface exposure module or system which overcomes one or more shortcomings of prior art devices. More particularly, the herein described modules and systems are based on a near laminar flow regime that mimics the fluid dynamics of the human lung. In addition the use of electrostatic precipitation for bipolarly or unipolarly charged particles ensures an efficient deposition of nanoparticles.

Provided herein is a flatbed air-liquid interface exposure module comprising a moisturizing section, an exposure section, and an aerosol duct, the aerosol duct being configured for sequentially guiding the charged nanoparticles through the moisturizing section and the exposure section. The flatbed air-liquid interface exposure module is further characterized in that the exposure section comprises a means for ensuring an electric field comprising a metal plate, which comprises a plurality of stubs which protrude from the metal plate into the exposure section.

In particular embodiments, the exposure section further comprises metal upper component. In these embodiments, the means for ensuring an electric field comprises the metal plate and the metal upper component. In these embodiments, the stubs protrude from the metal plate in the direction of the metal upper component.

In particular embodiments of the flatbed air-liquid interface exposure module provided herein, the moisturizing section comprising a water bath.

The flatbed air-liquid interface exposure module provided herein is particularly suitable for use with an inverted well set-up, which can be placed over the stubs. Accordingly, in particular embodiments of the flatbed air-liquid interface exposure module, the exposure section further comprises an inverted well cell culture set-up comprising one or more inverted wells, each inverted well comprising a porous membrane for supporting a plurality of cells at an air-liquid interface, the inverted wells being positioned over the stubs of the metal plate.

In particular embodiments, the flatbed air-liquid interface exposure module further comprises an insulating housing in the exposure section, whereby the insulating housing at least comprises an insulating lid which is placed over the inverted well culture set-up. More particularly, the insulating lid comprises a plurality of holes, whereby the holes are aligned with the inverted wells. In particular embodiments, the insulating lid is removable. In particular embodiments, the insulating housing is made of plastic or other insulating material. In particular embodiments, the insulating housing also encompasses the metal plate.

In particular embodiments of the flatbed air-liquid interface exposure module provided herein the exposure section further comprises a temperature controller. In particular embodiments, the temperature controller comprises one or more Peltier elements and a heat sink, the Peltier elements being thermally coupled to the heat sink. In particular embodiments, the exposure section is thermally isolated from the heat sink by means of a thermally insulating housing.

In particular embodiments, the flatbed air-liquid interface exposure module provided herein, further comprises one or more of a gravimetric sensor, a temperature sensor, and a humidity sensor.

In particular embodiments, the flatbed air-liquid interface exposure module provided herein further comprising a bridge between the moisturizing section and the exposure section.

The application also provides an air-liquid interface exposure system comprising a nanoparticle charging device, a fluidic system, a high voltage source and a flatbed air-liquid interface exposure module as described herein. More particularly, the nanoparticle charging device of the air-liquid interface exposure system is configured for charging nanoparticles in an aerosol comprising uncharged nanoparticles, thereby obtaining an aerosol comprising charged nanoparticles, the fluidic system of the air-liquid interface exposure system is configured for directing the aerosol comprising charged nanoparticles through the flatbed air-liquid interface exposure module, and the high voltage source is connected to the metal plate to ensure an electric field.

The application also provides methods for exposing a plurality of cells in vitro to nanoparticles comprised in an aerosol, using the air-liquid interface exposure systems and more particularly the flatbed air-liquid interface exposure modules described herein. These methods are of particular interest for nanotoxicity testing. In these methods, the cells are provided in the flatbed air-liquid interface exposure module and the aerosol comprising charged nanoparticles is allowed to pass through the flatbed air-liquid interface exposure module; in addition an electric field is generated in the exposure section of the flatbed air-liquid interface exposure module, so as to direct the charged nanoparticles aerosol to the cells. In particular embodiments, the cells are selected from the list consisting of airway epithelial cells and alveolar epithelial cells.

BRIEF DESCRIPTION OF THE FIGURES

The following description of the figures of specific embodiments of the methods and instruments described herein is merely exemplary in nature and is not intended to limit the present teachings, their application or uses.

Figure 1:
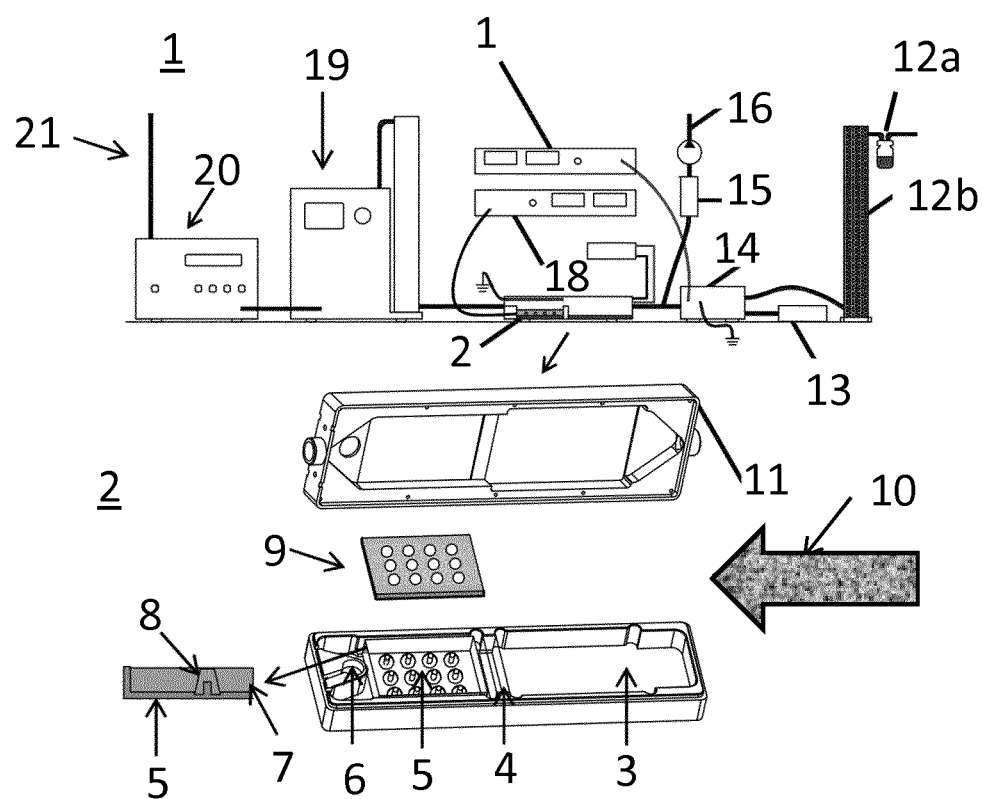
FIG. 1 shows an embodiment of an air-liquid interface exposure system (1) comprising an air-liquid exposure module (2) according to the invention.

Throughout the figures, the following numbering is adhered to: 1—air-liquid interface exposure system; 2—flatbed air-liquid interface exposure module; 3—water chamber; 4—bridge; 5—stainless steel plate; 6—quartz crystal microbalance; 7—cell culture medium; 8—inverted well cell culture set-up; 9—insulating lid; 10—aerosol flow indicator; 11—casing; 12a—atomizer; 12b—diffusion dryer; 13—filter; 14—corona jet charger; 15—mass flow controller; 16—exhaust; 17—high voltage source for corona jet charger; 18—high voltage source for flatbed air-liquid interface exposure module; 19—scanning mobility particle analyser; 20—condensation particle counter; 21—exhaust; 22—inlet; 23—outlet; 24—stubs; 25—cells; 26—insulating housing; 27—plate chamber; 28—exposure section; 29—moisturizing section.

DETAILED DESCRIPTION OF THE INVENTION

Before the systems and methods of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments.

Furthermore, while particular embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

Provided herein are air-liquid interface exposure systems and flatbed air-liquid interface exposure modules suitable for use therein. The exposure systems and modules are used for exposing a plurality of cells at an air-liquid interface to nanoparticles. In particular embodiments, the exposure system is a multi-component flatbed exposure device. The system described herein allows achieving a near laminar flow regime that mimics the fluid dynamics of the human lung and an electrostatic precipitation for bipolarly or unipolarly charged particles, and allows for improved deposition efficiency of nanoparticles.

The air-liquid interface exposure systems provided herein comprises a flatbed air-liquid interface exposure module, which typically comprises a moisturizing section, an exposure section, and an aerosol duct, which allows air to flow from the moisturizing section to the exposure section. During normal use, the module allows exposing cells to nanoparticles by using a horizontal aerosol flow over cells cultured in an inverted well cell culture set-up, and electrostatically depositing the nanoparticles on the cells, without the need for an amplified air stream.

In general terms, the operation of the flatbed air-liquid interface exposure module may be described as follows. An aerosol comprising charged nanoparticles is moved into the moisturizing section through an inlet in the moisturizing section. In the moisturizing section, the aerosol comprising charged nanoparticles is humidified to bring the relative humidity of the aerosol to physiological conditions such as found, for example, in the human lungs. The aerosol comprising charged nanoparticles, which is moisturized, is then moved to the exposure section. In the exposure section, charged nanoparticles are electrostatically pulled towards the cells by means of an electric field. The resulting aerosol (at least partially depleted of nanoparticles) is then vented through the outlet.

The present flatbed air-liquid interface exposure module allows closely mimicking the natural environment of cells where living cells are in contact with a liquid and a gaseous phase, such as in the human lung, even for long duration measurements (e.g. up to 16 hours). In the present systems and devices, alterations of the physicochemical properties of the nanoparticles are limited, and it is possible to accurately determine the dose of nanoparticles, which are administered to the cells. Thus, by providing an appropriate flow-rate through the flatbed air-liquid interface exposure module to correspond to that of a given flow pattern of the human lung (i.e. within a generation) deposition of nanoparticles can be mimicked. Accordingly, one of the uses of the devices and methods provided herein is providing realistic simulations of interactions between pulmonary cells and nanoparticles. Another use is rapidly and accurately assessing physical and immune effects related to airborne nanoparticles in human lungs.

The flatbed air-liquid interface exposure modules as provided herein comprise a moisturizing section, an exposure section, and an aerosol duct, which aerosol duct allows air to flow from the moisturizing section to the exposure section.

The exposure section of the flatbed air-liquid interface exposure modules as provided herein typically comprise a plate chamber, which allows positioning of a system on which the cells can be provided in an environment which ensures survival thereof at least during the exposure time required, such as a cultivation plate. More particularly the exposure section of the modules provided herein is designed to function with an inverted well cell culture set-up. The exposure section of the flatbed air-liquid interface exposure module provided herein comprises a metal plate comprising a plurality of stubs. In particular embodiments, the metal plate comprises a total of 6-18, preferably 12 stubs, i.e. discrete areas of the plate which extend from the metal plate into the exposure section, in particular discrete areas of the plate which extend in upward direction from the metal plate or vertically. The size and shape of the stubs is adjusted such that inverted wells may be positioned over the stubs. The stubs may enhance nanoparticle deposition on cells growing on inverted wells which may be positioned over the stubs, as will be explained in more detail below.

The flatbed air-liquid interface exposure modules provided herein further comprise a moisturizing section. The moisturizing section ensures that the air-flow which runs through it, is moisturized. Preferably, the moisturizing section comprises a water bath. Alternatively, the moisturizing section comprises a material, which retains water, such as a gel or a cloth, such as a felt. The moisturizing section allows moisturizing the aerosol comprising charged nanoparticles while minimizing nanoparticle losses. Using a water bath particularly allows reducing nanoparticle losses compared to systems, which use for example, a felt for humidification. During normal use, the water bath is generally filled with de-ionized water to humidify an aerosol stream passing over it.

In particular embodiments, the flatbed air-liquid interface exposure module comprises a bridge between the moisturizing section and the exposure section. The bridge is an essentially vertical structure between the moisturizing section and the exposure section. This enhances the air-flow through the flatbed air-liquid interface exposure module.

The flatbed air-liquid interface exposure modules provided herein further comprise an aerosol duct, i.e. a system, which sequentially guides an air stream with minimal turbulences, through the moisturizing and exposure sections.

More particularly the aerosol duct guides an aerosol comprising the charged nanoparticles, sequentially through the moisturizing section and the exposure section. Typically, the aerosol duct is ensured by an inlet positioned at one end of the flatbed air-liquid interface exposure module (in the moisturizing section) and an outlet positioned at the opposing end of the flatbed air-liquid interface exposure module (in the exposure section).

Preferably, the aerosol duct guides the aerosol comprising charged nanoparticles horizontally over the plurality of inverted wells when these are placed in the exposure section. This allows laminar flow of the aerosol comprising charged nanoparticles over the inverted wells, which enhances nanoparticle deposition. Moreover, in particular embodiments, the flow of the aerosol duct can be adjusted such that the cells can be contacted with the aerosol over a wide range of flow velocities.

The term "horizontal" as used herein includes orientations which deviate from the horizontal plane by less than 10°, preferably by less than 5°, more preferably by less than 1°.

In particular embodiments, the aerosol duct comprises an aerosol tunnel in the humidifying section. In particular embodiments, the tunnel is made of a semi-permeable plastic membrane. The tunnel allows minimizing turbulences of the airflow.

In particular embodiments, the aerosol duct does not comprise a tunnel in the humidifying section.

In particular embodiments, the plate chamber of the exposure section is configured to function as a water bath. This facilitates temperature control in the exposure chamber. In alternative embodiments, the plate chamber does not comprise water.

In particular embodiments, the exposure section comprises a temperature controller. This allows to accurately control the conditions within the exposure section. Preferably, the temperature controller comprises one or more, preferably about 10 Peltier elements and a heat sink. The Peltier elements are thermally coupled to the heat sink. Accordingly, heat can be added to, or removed from, the exposure section as desired.

In particular embodiments, the power of each Peltier element is between 50 and 150 W, preferably between 75 and 125 W, more preferably about 95 W.

Preferably, the Peltier elements are evenly distributed on the top and bottom side of the exposure section. This can enhance temperature uniformity in the exposure section.

In particular embodiments, the flatbed air-liquid interface exposure module comprises a plurality of sensors. These sensors may include a gravimetric sensor (e.g. a quartz crystal microbalance, for example a quartz crystal microbalance sensitive down to the ng-range), a temperature sensor, and a humidity sensor.

In particular embodiments, the flatbed air-liquid interface exposure module comprises one or more temperature sensors for monitoring the internal temperature in the flatbed air-liquid interface exposure module. The one or more temperature sensors may be operably coupled to a controller, which is configured for comparing one or more measured temperatures with a preset temperature. When the measured temperature is lower than the pre-set temperature, the flatbed air-liquid interface exposure module may be heated by means of the one or more Peltier elements until the preset temperature is reached. When the measured temperature is higher than the pre-set temperature, the flatbed air-liquid interface exposure module may be cooled by means of the one or more Peltier elements until the preset temperature is reached.

In particular embodiments, the flatbed air-liquid interface exposure module is provided by a power supply comprising a constant-current controller. The constant-current controller may enable fine-tuning of the target temperature, which can minimize electromagnetic noise. Electromagnetic noise can be an issue with standard controllers. Minimizing electromagnetic noise allows eliminating signal interface interference with built-in sensors.

The flatbed air-liquid interface exposure module may further comprise one or more of a gravimetric sensor (e.g. a quartz crystal microbalance, for example a quartz crystal microbalance sensitive down to the ng-range) and/or a humidity sensor. In particular embodiments, sensors are used for monitoring air quality within the flatbed air-liquid interface exposure module and/or for monitoring nanoparticle deposition. In particular embodiments, the sensors are positioned between the exposure section and an outlet for venting nanoparticle-depleted aerosol from the exposure section. The sensors can help to ensure that the environmental parameters within the flatbed air-liquid interface exposure module may be optimally measured such that cells can be optimally maintained. Also, the sensors allow monitoring reproducibility within different runs after the deposition area, so thereby ensuring that the nanoparticles are adequately deposited onto the cells.

In particular embodiments, one or more gravimetric sensors are configured for monitoring direct deposition of nanoparticles into the cell culture medium. This is a very efficient monitoring method. In particular, it is much more efficient than more elaborate techniques such as inductively coupled plasma mass spectrometry (ICP-MS).

In particular embodiments, the flatbed air-liquid interface exposure module further comprises a chassis, preferably a metal chassis, more preferably an anodized aluminum chassis. The chassis may provide mechanical support for the various components of the flatbed air-liquid interface exposure module.

As indicated above, the flatbed air-liquid interface exposure module and air-liquid interface exposure system provided herein is particularly suitable for use with an inverted well culture set-up. Accordingly, in particular embodiments, and specifically during normal use of the present air-liquid interface exposure system and modules provided herein, the exposure section comprises an inverted well cell culture set-up. The inverted well cell culture set-up comprises a plurality of inverted wells. Each inverted well comprises a porous membrane for supporting a plurality of cells. One suitable type of inverted well, for use as provided herein, are Transwell Permeable Supports (Corning). In particular embodiments, the inverted wells comprise cells, which are positioned on top of the membranes of the inverted wells.

For exposure of the cells to the aerosol, the inverted wells are positioned over the stubs of the metal plate in the exposure section of the flatbed air-liquid interface exposure module, such that each inverted well fits over a stub. During normal operation, the plate chamber comprising the steel plate with stubs is provided with growth medium, such that the growth medium reaches the porous membranes, which allows growth of the cells on the membranes.

The exposure section of the flatbed air-liquid interface exposure module is configured to maintain an electric field. More particularly, the module comprises a means for ensuring an electric field. In particular embodiments, the means comprises the metal plate, which is connected to a high voltage source. The electric field directs charged nanoparticles present in the air-flow in the exposure section towards the porous membranes on the inverted wells. In further particular embodiments, the means for ensuring an electric field comprises, in addition to the metal plate, a second component which is an upper metal component placed above the aerosol duct; In particular embodiments, the upper component is a metal plate. Accordingly, in these embodiments, the electric field is generated by means of a bottom metal plate which is connected to a voltage source and the metal upper component (e.g. an insulated upper electrode or a metal lid) which is placed above the aerosol duct. In particular embodiments, the metal upper component is grounded, e.g. by means of a grounded counter electrode. In further particular embodiments, the grounded counter-electrode is integrated into the upper component. In alternative embodiments, the upper metal component is connected to a positive or negative HV, and the bottom metal plate is grounded.

In particular embodiments, the metal upper component positioned above the aerosol duct is a metal top lid.

In these embodiments, an electric potential difference is generated between the bottom metal plate and the metal component placed above the aerosol duct, the gradient of the electric potential corresponding to the electric field, and the electric field causing an electrostatic force on charged nanoparticles. This electrostatic force directs the charged nanoparticles towards the metal plate and thus towards the cells.

The air-liquid interface exposure system provided herein is typically used to detect the effect of nanoparticle deposition on cells. Preferably, the nanoparticles are positively charged. Accordingly, the nanoparticles may be efficiently directed to cells, which grow on the porous membranes. This allows an excellent deposition rate, which allows working with aerosols comprising a relatively low concentration of nanoparticles.

The present inventors could show that the electric field does not induce a stress reaction in cells growing at the air-liquid interface, such as cells of lung cell line A549.

In particular embodiments, the exposure section is configured to ensure a voltage between the metal upper component (e.g. top lid) and the bottom metal plate, for example a voltage of −1 kV. In particular embodiments, the metal plate is electrically connected to a voltage source. Typically, the metal plate is brought at a negative potential with respect to the metal upper component, such that positively charged nanoparticles are electrostatically attracted to the metal plate. Alternatively, the metal plate is brought at a positive potential with respect to the metal upper component, such that negatively charged nanoparticles are attracted to the metal plate. However, the polarity should be consistent with the charge of the nanoparticles: when the nanoparticles are positively charged, the metal plate should be at a negative potential with respect to the metal upper component. When the nanoparticles are negatively charged, the metal plate should be at a positive potential with respect to the metal upper component.

Preferably, the High Voltage unit connected to the metal plate is grounded, and the metal upper component positioned above the aerosol duct (e.g. the metal top lid or an upper metal grid) acts as a grounded counter electrode. This reduces the risk of electric shock.

In particular embodiments, the potential difference between the metal plate and the metal component positioned above the aerosol duct is provided by a high voltage source, which is galvanically separated from a main power supply.

Accordingly, the exposure section is equipped with an electric field for directing charged nanoparticles to the plurality of cells at the liquid-air interface. The metal plate's stubs below the porous membranes of the inverted wells may act to concentrate electric field lines on the porous membranes, which enhances nanoparticle deposition on cells growing on the porous membranes.

In particular embodiments, the flatbed air-liquid interface exposure module further comprises an insulating housing at least partially enclosing the metal plate. This improves thermal behavior and stabilization and it can enhance temperature control in the exposure section. The housing typically comprises at least a bottom section, which fits around the metal plate.

Additionally or alternatively, the housing encloses the top part of the metal plate with the inverted well cell culture set-up, such as by way of an insulating lid. The insulating lid may or may not be a part of the insulating housing. The insulating lid comprises a plurality of holes and may be positioned on the metal plate such that the holes in the insulating lid are aligned with the stubs on the metal plate. Preferably, the number of holes is equal to the number of stubs. This allows more efficiently directing the nanoparticles to cells and reduces losses to the metal plate itself. In particular embodiments, the diameter of the holes in the insulating lid is 12 to 15 mm. In particular embodiments, the insulating housing is made of polystyrene or other insulating material. In particular embodiments, the insulating lid is removable. This allows easy access to the metal plate and to the inverted well cell culture set-up.

In particular embodiments, the insulating housing is fully closed which enhances the electrical insulation of the metal plate. The insulating housing provides electrical insulation between the metal plate and other parts of the flatbed air-liquid interface exposure module, e.g. the water bath in the moisturizing section and/or the flatbed air-liquid interface exposure module's housing. In particular embodiments, the insulating cover comprises plastic. Preferably, the insulating cover is made of an insulating material with a sufficiently high dielectric constant. In particular embodiments, the insulating cover is made of polystyrene.

In particular embodiments, the flatbed air-liquid interface exposure module comprises a casing, which covers at least the exposure section, but typically covers both the exposure and the moisturizing section. Preferably, the casing is made of an insulating material.

Further provided herein is an air-liquid interface exposure system comprising the flatbed air-liquid interface exposure module described above. Typically, the air-liquid interface exposure system additionally comprises a nanoparticle charging device and a fluidic system. The nanoparticle charging device is configured for accepting an aerosol comprising uncharged nanoparticles, and for charging the nanoparticles so as to generate an aerosol comprising charged nanoparticles. The fluidic system is configured for directing the aerosol comprising charged nanoparticles to the flatbed air-liquid interface exposure module. Generally, the fluidic system is configured for directing the aerosol comprising charged nanoparticles to an inlet in the moisturizing section. Also, the fluidic system is generally configured for venting the aerosol from the exposure section via an outlet, after the aerosol has passed through the flatbed air-liquid interface exposure module and has been (at least partially) depleted of nanoparticles by means of the electric field therein.

In particular embodiments, the nanoparticle-charging device comprises a collison-type atomizer, a drier, an air filter, and a corona charger. The collison-type atomizer may be fed by a nanoparticle suspension. In particular embodiments, the nanoparticle suspension is prepared by sonication in a sonication device. The collison-type atomizer may be used for atomizing the aforementioned nanoparticle suspension, and for thus producing a nanoparticle-bearing air stream, which may retain a significant amount of moisture. In particular embodiments, the nanoparticle-bearing air stream is dried, for example by means of a diffusion or Nafion drier. The dried nanoparticle-bearing air stream may be mixed with an ionized air stream. In particular embodiments, the ionized air stream is ionized by means of a corona charger, and is purified by means of an active carbon filter and a HEPA filter prior to ionization. Through mixing the dried nanoparticle-bearing air stream and the ionized air stream, an aerosol comprising charged nanoparticles is obtained which is fed to the flatbed air-liquid interface exposure module.

In particular embodiments, the exhaust of the flatbed air-liquid interface exposure module is operationally connected to a scanning mobility particle sizer, which may include a condensation particle counter, a neutralizer and a dynamic mobility analyser.

This allows excellent monitoring of the operation of the flatbed air-liquid interface exposure module.

Additionally or alternatively, the exhaust of the exposure module is sequentially connected to a pump connected to a mass flow controller (MFC).

Accordingly, in particular embodiments the air-liquid interface exposure system comprising the flatbed air-liquid interface exposure module described herein, a nanoparticle charging device comprising a collison-type atomizer, a drier, an air filter, and a corona charger, a High Voltage unit connected to the metal plate, control units for controlling temperature and relative humidity, a scanning mobility particle sizer (SMPS) and an exhaust which is connected to a pump connected to a mass flow controller (MFC).

Further provided herein are methods for exposing a plurality of cells in-vitro to nanoparticles. The present methods particularly allow laminar flow nanoparticle deposition on cells grown on inverted wells.

In the methods provided herein, the nanoparticles are comprised in an aerosol, and the method involves the use of a flatbed air-liquid interface exposure module as provided herein. As detailed above, the flatbed air-liquid interface exposure module comprises a moisturizing section and an exposure section. The exposure section is configured for use with an inverted well cell culture set-up comprising inverted wells for supporting cells at an air-liquid interface. The inverted wells are positioned over the stubs of the metal plate. The plate chamber is filled with medium up to the cell membrane of the inverted wells. This ensures that the cells are positioned at an air-liquid interface.

The methods provided herein typically comprise passing an aerosol comprising charged nanoparticles through the areal duct in the flatbed air-liquid interface exposure module, and applying an electric field in the exposure section, so as to expose the cells to the nanoparticles.

When performing the method, the aerosol comprising charged nanoparticles is moved first into the moisturizing section. In the moisturizing section, the aerosol comprising charged nanoparticles is humidified. Accordingly, a moisturized aerosol comprising charged nanoparticles is obtained. Subsequently, the moisturized aerosol comprising charged nanoparticles is moved to the exposure section. In the exposure section, an electric field is used to direct the charged nanoparticles to a plurality of cells at the air-liquid interface. The charged nanoparticles are intercepted by the plurality of cells present on the inverted wells at the air-liquid interface.

The moisturized aerosol (at least partially) depleted of nanoparticles is then vented out of the module. Though the above method is described as a consecutive sequence of steps, it will be appreciated that the method is in practice executed as a continuous process.

As explained elsewhere, the inverted wells are positioned on the stubs of the metal plate. An inverted well typically comprises a porous membrane on which the cells can grow. A culture medium is provided in the plate chamber such that the fluid level corresponds to the level of the porous membranes. Accordingly, cells growing on the porous membrane may be provided with nutrients by means of the culture medium, while the cells may concurrently be exposed to nanoparticle-containing air in the exposure section.

In particular embodiments, the cells are cells selected from the list consisting of airway epithelial cells and alveolar epithelial cells. The electrical field does not cause a stress reaction for certain lung cells, such as cells of cell line A549.

Preferably, the electric field is maintained at a pre-determined electric field strength, which depends on the diameter of the nanoparticles, that need to be deposited. Generally, the smaller the nanoparticles, the larger the electric field strength for the same deposition rate. In particular embodiments, the flatbed air-liquid interface exposure module is configured to generate an electric field by means of a potential difference between the metal plate and the metal component which is placed above the aerosol duct, the potential difference being between 0 and 2 kV, preferably between 0.50 and 1.5 kV, the potential difference more preferably being about 1.0 kV.

Generally, the charge applied to the nanoparticles depends on the size of the nanoparticles. More specifically, a smaller charge is generally applied to smaller particles with a smaller surface area compared to larger particles with a larger surface area. In particular embodiments, a charge between 1 and 100 nC is applied to nanoparticles smaller than 1 μm; see for example Telko M J (2009) Investigation of Electrostatic Charging Phenomena in dry Powder Inhalers and the effect on deposition; PhD-Thesis, University of North Carolina.

Preferably, the flow velocity of the air stream comprising the nanoparticles is adjusted to the deposition regime, which is investigated. In particular embodiments, the flow velocity is smaller than 0.001 cm/s. This allows investigating deposition in alveolar flows. In particular embodiments, the flow velocity is about 40 cm/s. This allows investigating deposition in bronchial flows.

The present methods allow simple, rapid detection of physical and in vitro immune effects of nanoparticles. In particular embodiments, the methods comprise determining the effect of nanoparticles present in an aerosol on cell viability. In particular embodiments, cells are provided with a reporter gene and viability is assessed based on luminescence of the cells.

Accordingly, the application provides methods for determining the effect of nanoparticles on a cell, which methods involve the steps of contacting the cell with the nanoparticles as described hereinabove and analyzing the cells thereafter. Typically the cell is compared to a cell, which has not been contacted with the nanoparticles. The application further provides methods for identifying compounds capable of mitigating the effect of nanoparticles on a cell, which methods involve the steps of contacting the cell with the nanoparticles as described hereinabove, in the presence or absence of said compound, and analyzing the cells thereafter.

The systems provided herein provide a model system for determining the effect of nanoparticles on a mammalian lung, such as a human lung. Thus, in particular embodiments, the methods and devices can be used to determine the effect of aerosolized nanoparticles on lung cells.

EXAMPLES

Example 1: Air-Liquid Interface Exposure System According to an Embodiment of the Invention In a first example, reference is made to FIG. 1. FIG. 1 shows a particular embodiment of an air-liquid interface exposure system (1) built around a flatbed air-liquid interface exposure module (2).

The nanoparticles are generated using a collision-type atomizer (12a) and charged before they are brought into the flatbed air-liquid interface exposure module (2) as an aerosol. In particular, the nanoparticles leaving the atomizer are dried using a diffusion dryer (11). The nanoparticles are then charged by mixing with compressed air passed through a carbon and HEPA filter (13) and charged in a corona jet charger (14). The system further comprises a mass flow controller (15), and an exhaust (16). The workings of the nanoparticle charging device are explained in more detail elsewhere.

The flatbed air-liquid interface exposure module (2) in this embodiment comprises a water bath (3), a bridge (4), a stainless steel plate (5), and a quartz crystal microbalance (6). The stainless steel plate (5) comprises a plurality of stubs which protrude upwardly from the metal plate and supports cell culture medium (7) providing nutrients for cells growing on porous membranes of inverted well (8), above stubs of the stainless steel plate (5). A polystyrene lid (9) comprising a plurality of holes is provided to cover the medium comprising the inverted well cell culture set-up except where cells grow on the porous membrane of the inverted well. A high-voltage source for the flatbed air-liquid interface exposure module provides 1 kV between the stainless steel plate (5) and the casing (11), which is grounded. This configuration allows effective electrostatic deposition of nanoparticles on the cells.

After the aerosol has passed the flatbed air-liquid interface exposure module (2), it is depleted of nanoparticles, most of which were deposited on the cells. The nanoparticle-depleted aerosol is subsequently directed to a scanning mobility particle analyser (19) and to a condensation particle counter (20) for further characterization. Then, the nanoparticle-depleted aerosol is vented via an exhaust (21).

Example 2: Implementation of an Air-Liquid Interface Exposure System According to an Embodiment of the Invention Aerosolization Setup Nanoaerosols were generated using a collison-type atomizer containing a 50 ml CuO suspension and HEPA-filtered pressurized air (5 bar). Synthetic CuO-NPs of 22-25 nm (Nanologica AB) were mixed with MilliQ water to prepare a CuO-NPs suspension (4 g/l). The suspension was sonicated in conformity with the standard operating procedure (SOP) "Dispersion of NNV-011 (CuO) nanoparticle suspensions for toxicological testing" developed by the NanoValid consortium. The sonicated suspension was directly used for atomization. The NP-containing air-flow leaving the atomizer (4 liters per minute, lpm) was dried using a diffusion dryer. A second air-flow of 1 lpm pressurized air passed through a carbon and HEPA filter (HEPA/C) and an ionizer (corona jet charger, CC, at +2.5 kV). Both flow streams were merged in a mixing chamber where particles in the aerosol flow are mixed with the positive ions carried by the filtered clean air. Using a T-split 0.3 lpm of the charged aerosol flow entered the exposure chamber, while 4.7 lpm were led into the exhaust of the fume hood using a pump connected to a mass flow controller (MFC). The exhaust of the exposure chamber was connected to a scanning mobility particle sizer (SMPS) including the condensation particle counter (CPC) operating at a sample flow of 0.3 lpm.

Exposure System

A prototype of the flatbed air-liquid interface exposure module (45 cm long, 11 cm width, 5.5 cm height) was constructed of an anodized aluminium chassis. Temperature control was achieved by ten evenly distributed Peltier elements (PE) on the top and bottom side of the flatbed air-liquid interface exposure module. The PE-elements were operated either in heating- or cooling-mode via an external controller with a built-in temperature sensor. To assure stable thermal conditions (36-37° C.), the flatbed air-liquid interface exposure module was embedded into ruggedized polyethylene housing, allowing only the PE-elements to be in contact with the outside mounted heat sink. The top plate could be removed for easy access to the inverted well cell culture setup and water bath. The inside of the flatbed air-liquid interface exposure module consisted of three compartments: the first compartment after the aerosol inlet represented a water bath, filled with Milli-Q water, to humidify the aerosol stream passing through a semi-permeable membrane-guided aerosol tunnel at its front, lateral and tail edges well-fitted to the inner walls of the flatbed air-liquid interface exposure module to ensure a laminar flow of the aerosol; the second compartment was designed to house a stainless steel (SS) 12-well plate containing cell culture medium (CCM); towards the exit of the flatbed air-liquid interface exposure module, a gravimetric sensor (quartz crystal microbalance, QCM) was fitted into the metal chassis along with a temperature and humidity sensor to monitor air quality inside the flatbed air-liquid interface exposure module. Temperature, relative humidity (rH), and mass-data were logged via an Arduino-based software interface to an external computer.

To enable electrostatic field-assisted deposition of the positively charged CuO nanoaerosols onto the inverted transwell cell-inserts, the SS 12-well plate was connected to a high voltage (HV) source (−1 kV, 0 A). An grounded electrode was mounted into the top-lid directly above the 12-well plate. For electric insulation from the water bath and the aluminium housing, the SS 12-well plate was placed into a polystyrene (PS) tub. To shield the CCM-containing SS 12-well plate from the charged CuO nanoaerosol, a PS top-lid with twelve 15 mm holes was used.

Nanoaerosol Characterization

A scanning mobility particle sizer (SMPS) was used to measure size distribution of the aerosolized CuO-NPs. The used model 3936 consists of an electrostatic classifier model 3080, a neutralizer model 3077 consisting of a Krypton-85 source (370 MBq), a long differential mobility analyzer (DMA) model 3081, and a butanol-based condensation particle counter (CPC) model 3025A, all from TSI Inc., USA. The SMPS combines particle size classification according to the article mobility diameter followed by measurement of the concentration by using a CPC, which operates on the principle of enlarging small particles by means of a condensation technique to form droplets that are large enough to be detected optically. The CPC was adjusted to a size range between 15 nm and 661 nm, a scan time of 100 seconds, a retrace time of 15 seconds and a 2 minute recurrence interval.

Cell Lines

Two A549 (human alveolar epithelial lung carcinoma) reporter cell lines were used, possessing a luciferase reporter gene under the regulation of the promoter of interleukin (IL-8) or under regulation of four copies of the nuclear factor kappa B (NFκB) response element. The establishment of these cell lines has been described in detail in Oostingh, G. J.; Schmittner, M.; Ehart, A. K.; Tischler, U.; Duschl, A. Toxicol In Vitro. 2008, 22 522 (5), 1301-1310.

Cell Culture Conditions

All cells were cultured at 37° C. in a humidified incubator with 5% CO2. The transfected cell line pIL8-luc A549 was cultured in RPMI 1640, supplemented with 1% L-glutamine, 100 U/ml penicillin, 100 µg/ml streptomycin (all from Gibco), 10% foetal bovine serum (FBS, gold serum, Biochrom), and 1% G418 sulphate (500 µg/ml, Invivogen) as selection antibiotic. The NFκB-luc A549 transfected cells were purchased from Panomics (Affymetrix, Inc.) and cultured according to the distributor's description in Dulbecco's Modified Eagle's Medium with L-glutamine and without sodium pyruvate (Gibco), supplemented with 100 U/ml penicillin, 100 µg/ml streptomycin, 10% FBS and 100 µg/ml 205 hygromycin B (Roche). Before seeding, cells were rinsed once with phosphate buffered saline (PBS, Gibco), detached by trypsinization (0.25% trypsin-EDTA, Gibco), and counted. ThinCert 24-well cell culture inserts (1 µm pore size, PET membrane; Greiner) were put upside-down in a Petri dish and 50 µl of cell suspension ($2 \times 10^5$ cells/ml, i.e. $1.0 \times 10^4$ cells/insert) was put on the membrane of the insert. The Petri dish was covered and inserts were incubated in a humidified incubator at 37° C. with 5% $CO_2$. After 2.5 hours, membranes were carefully washed with PBS (containing calcium$^{2+}$ and magnesium$^{2+}$) and inserts were placed in a 24-well plate in a normal hanging position. A549 medium was added to the lower (800 µl) and upper (100° µl) compartment and cells were left to grow for 2 days under submerged conditions to form a confluent monolayer.

Transfer to Air-Liquid Interface (ALI) for Exposure to Nanoparticles.

An in house-constructed stainless steel (SS) 12-well plate consisting of 12 positions for inverted wells (i.e. technical replicates) was filled with 100 ml A549 medium. Twelve inserts (i.e. inverted wells) were placed on the plate in inverted position (upside-down) at ALI. The medium in the 12-well plate was supplemented (20 ml) avoiding overflow on the inserts and the flatbed air-liquid interface exposure module was closed. For each analysis (i.e. Cu quantification using ICP-MS, cell viability, pro-inflammatory potential), 12 well inserts were exposed to clean air (negative control), to 12 ppm $NO_2$ (positive control for cell viability), and to 4 g/l CuO-NPs for an exposure period of 1 hour (0.3 lpm, +2.5 kV corona charger, −1.0 kV HV). Temperature and relative humidity (rH) during exposure were monitored and were found to be stable at 36-37° C. and 99% rH. After 1 hour exposure, the biological endpoint measurements and Cu quantification were performed. Three independent biological experiments using different passages of the cell lines and freshly made CuO—NP suspensions were performed.

At least 3 incubator controls were included in each biological experiment. For this, inserts were placed in a humidified incubator for 1 hour in inverted position in a 12-well plate containing 5.5 ml/well. The same setup was used to add tumor necrosis factor-alpha (TNF-232 a, Roche; 250 ng/ml for pIL8 luc, 25 ng/ml for pNFλB-luc cells) in the medium of at least 3 other inserts as positive control for the luciferase reporter gene (LUC) assay.

Cell Viability

Cell viability was assessed using the CellTiter-Blue® cell viability assay kit (Promega). This assay is based on the ability of viable cells to convert the blue redox dye resazurin into the fluorescent compound resorufin whereas non-viable cells do not produce any fluorescent signal. For this assay, all 12 inserts were post-incubated (submerged) for 20 hours in 450 µl A549 medium containing CellTiter-Blue® Reagent in a 24-well plate. At the same time, 50 µl of this reagent was also added in the insert. After 20 hours incubation in a humidified incubator, both reagents were mixed and 120 µl was transferred to a white 96-well plate (in triplicate). Fluorescence was recorded at 544/590 nm using a plate reader (Fluoroscan Ascent).

Immune Effects

The pro-inflammatory potential was assessed using two stably transfected A549 cell lines as previously described in Oostingh, G. J.; Schmittner, M.; Ehart, A. K.; Tischler, U.; Duschl, A. Toxicol In Vitro. 2008, 22 522 (5), 1301-1310. For the LUC assay, inserts were 2.5 hour post-incubated (submerged) in a 24-well plate containing A549 medium (800 µl in lower compartment, 50 µl in upper compartment) in a humidified incubator. After post-incubation, the remaining medium was removed. Cells were lyzed by adding 350 µl reporter lysis buffer (Promega) in each well and 50 µl reporter lysis buffer was added in the hanging inserts. After shaking plates for 25 minutes at room temperature, plates were frozen (−80° C.) for minimum 1 hour and maximum 1 week. After thawing the plates at room temperature, reporter lysis buffer (in well+insert) were mixed and 40 µl was added to a white 96-well plate (in triplicate). Luminescence was measured for 5 seconds using a luminometer (Luminoskan) after injection of an equal amount of luciferase reagent (Promega) in each well.

Statistical Analysis

A two-way ANOVA with repeated measures was applied to test the statistical difference between clean air and CuO—NP exposure and between clean air and $NO_2$ exposure. The model takes into account the three independent biological experiments and the 12 different inserts (i.e. technical replicates) on the SS plate for each tested condition (=full plate analysis). This is also called 'treatment within subjects' design with clean air, CuO—NP, and $NO_2$ as the treatments and the 12 inserts as the subjects. This method was chosen because the position of the 12 inserts is determinative for the resulting cell viability outcome.

A straight two-way ANOVA model was applied to test the statistical difference between incubator control and clean air and TNFα exposure, since there is no link between the positions in the flatbed air-liquid interface exposure module and only a few data is available for the incubator control (at least 3 inserts tested). For this, the model only takes into account the independent biological experiments and flow information. All statistical analyses are done using R.

From ICP-MS determination it was found that deposition of CuO—NP was significantly less in the second half of the SS plate. For this reason, statistical difference between clean air and CuO—NP exposure was also determined for the first two exposed columns of the plate for comparison. In addition, a preferred air flow was noticed for the row in the middle of the plate showing high to lower Cu concentrations upstream to downstream. Statistics were also run for this specific row 'B'.

Results

A set of proof-of-principle experiments were performed with an air-liquid interface exposure system according to an embodiment of the invention.

In particular, the air-liquid interface exposure system was used for determination of biological responses to nanoaerosols. As a proof-of-principle for pro-inflammatory monitoring, two human alveolar epithelial A549 reporter cell lines were exposed to a model nanoaerosol of CuO-NPs. Efficient deposition from the laminar air flow was mediated by electrostatic field and the effect on cell viability and pro-inflammatory potential was analyzed.

Figure 2:
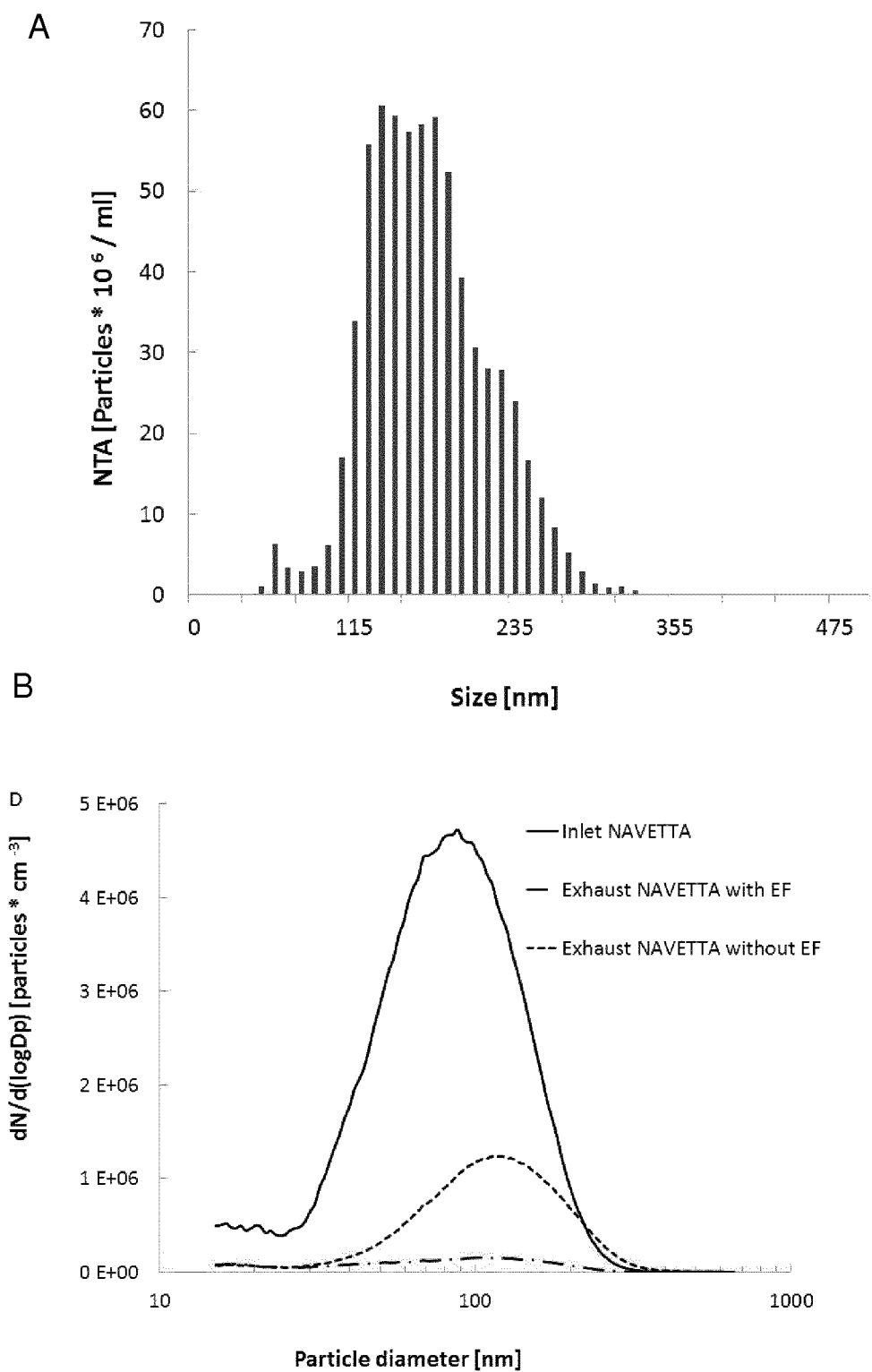
FIG. 2 shows the physicochemical characteristics of bulk material, more particularly the CuO-NPs dispersion as determined by NTA (A) and the generated aerosol expressed as difference between particle size distribution at the inlet and exhaust of the exposure chamber using SMPS (B).

The bulk material of CuO powder used for generating the nanoaerosol was characterized by a set of physico-chemical methods based on standardized protocols. The powder contained submicron-sized NP agglomerates consisting of single primary particles of 22-25 nm, with a surface area of 28 $m^2/g$ and a purity of >99% (with minor Ba and Ag contaminations). A standardized ultrasonic dispersion of CuO powder (4 g/l) was prepared following a standard operating procedure (SOP) accordingly and used for atomization. In the CuO dispersion the same primary particle size was observed, zeta potential measurements resulted in +35.9±1.3 mV, and DLS gave a z-average diameter of 154.5±1.7 nm with a polydispersity index of 0.157. This was found to be in good agreement with a mean particle size of 168.4±3.9 nm by NTA (FIG. 2A).

The nanoaerosol generated was charged and guided through the flatbed air-liquid interface exposure module for electrostatic field-mediated deposition onto cells. Particle deposition inside the flatbed air-liquid interface exposure module was determined indirectly by scanning mobility particle analyser measurements before and after the nanoaerosol entered the chamber. FIG. 2B shows the difference in particle size distribution at the inlet and exhaust of the exposure chamber with and without EF applied. The mean electrical mobility diameter was 89.1±3.3 nm at the inlet, 122.0±4.7 nm at the exhaust without EF applied and 102.0±7.5 nm at the exhaust with EF applied. At the inlet, number concentrations of 2.7±0.3×$10^6$ particles*$cm^{-3}$ were measured compared to 6.7±1.5×$10^5$ without EF and 1.3±0.5×$10^5$ particles*$cm^{-3}$ with EF at the exhaust. Thus, deposition efficiency was approximately 95% when the EF was applied, whereas approximately 75% of the particles at the inlet deposited without application of the EF.

Opening the flatbed air-liquid interface exposure module after 1 hour exposure revealed some degree of spatial variability of CuO among the 12 positions (FIG. 3A). This was also confirmed by direct quantification using inductively coupled plasma mass spectroscopy (ICP-MS) (FIG. 3B). Highest total Cu concentrations were measured at the column that was reached first by the aerosol flow (column 4). All three rows (A, B, C) experienced decreasing Cu concentrations with aging flow. A preferred air flow was noticed for the row in the middle showing highest Cu concentrations at all four columns (1-4). Scanning transmission electron microscopy (STEM) images confirmed these measurements showing extensive deposition of CuO-NPs on the membrane. Submicron-sized CuO—NP agglomerates were deposited or formed after impaction and a rather homogenous deposition was found on the grid.

The temperature and rH values varied within a certain range as a result of opening the flatbed air-liquid interface exposure module for inserting the A549 reporter cells. Immediately upon cell culture assembly, typically minimum temperature values of >33° C. were determined in the air compartment of the flatbed air-liquid interface exposure module, whereas the cell culture medium (CCM) and water bath kept approximately 37° C., and thus, the temperature in the aerial compartment adjusted quickly after closing. Approximately 30 minutes after closing the flatbed air-liquid interface exposure module, rH values of 99.9% were reached. The following experimental exposure conditions were used: 1 hour particle deposition at the ALI (inverted well cell culture set-up) followed by post-exposure incubation under submerged conditions in the cell culture incubator (20 hours for cell viability, 2.5 hours for pro-inflammatory potential).

Figure 4:
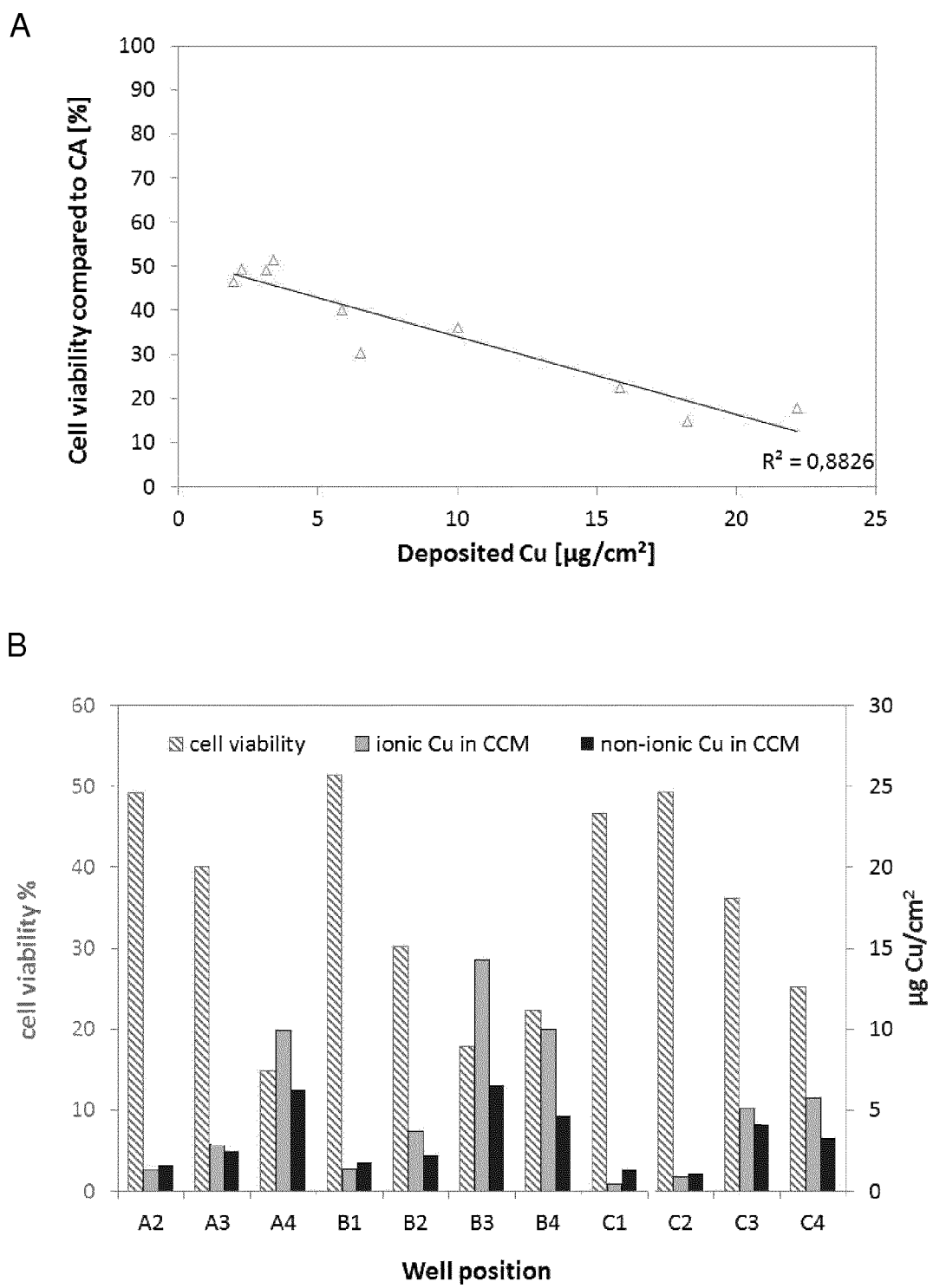
FIG. 4 shows the scatter plot relating % cell viability of NFκB-luc cells relative to clean air (CA) to total amount of deposited Cu in cell culture medium (CCM) after 20 hours post-exposure incubation (A); total amounts of Cu deposited on membrane (M), or present in CCM, and % cell viability per position (B); amounts of ionic and non-ionic Cu deposited in CCM and % cell viability per position (C); scatter plot relating cell viability of NFκB-luc cells and amounts of ionic (open circles, solid regression line) and non-ionic (open squares, broken regression line) Cu deposited in CCM after 20 hours post-exposure incubation (D).
Figure 4:
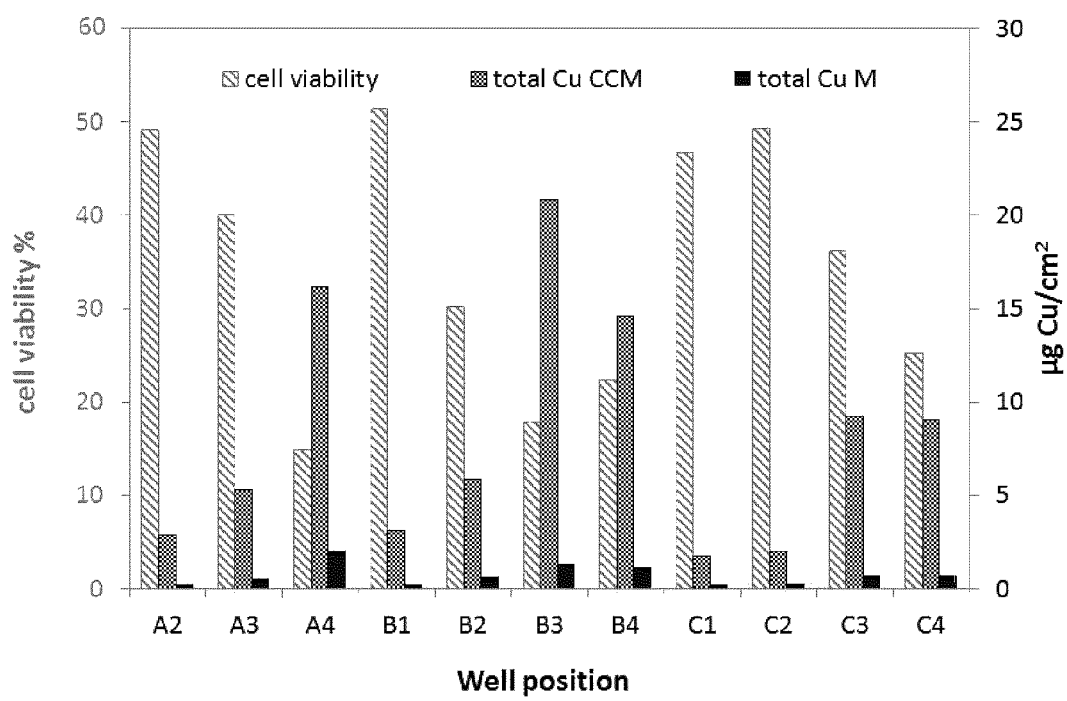
Figure 4:
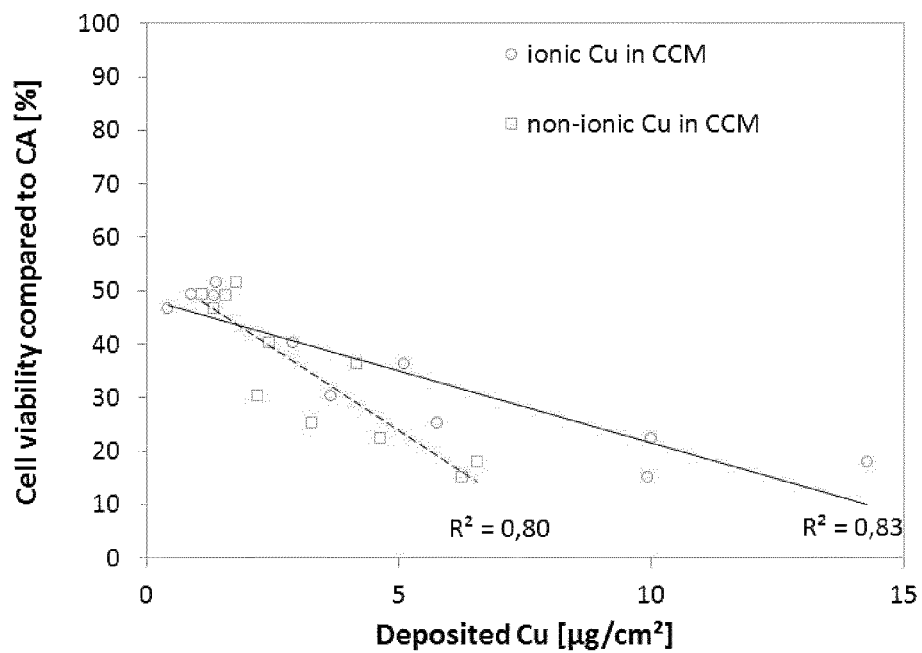

When exposing the cells to a CuO nanoaerosol flow, a decrease in cell viability of NFκB-luc cells was observed, which correlated strongly with the increasing amount of deposited CuO material, as determined by ICP-MS ($R^2$=0.88; FIG. 4A). The deposited total Cu concentration ($\mu g/cm^2$) on an inverted well membrane (M) was found to be lower than the CCM Cu concentration (FIG. 4B) after 20 hours post incubation. This suggests that large amounts of deposited CuO on the cells were not taken up by the cells, but adsorbed at their cell membrane and transferred to the CCM during post-incubation. The amount of Cu ions released by nano-CuO into the CCM are presented in FIG. 4C. Increasing total Cu concentrations resulted in increasing Cu ion concentrations in the CCM. Whether Cu ions reduce cell viability to a higher extent than non-ionic Cu could not be determined from the data shown in FIGS. 4C and D. Notably, there was a slight but negligible difference in correlation of the decreased cell viability and ionic versus non-ionic Cu concentration.

Figure 3:
FIG. 3 shows the spatial distribution of material deposited within 1 h on to inverted wells as captured by photographic imaging according to an embodiment of the invention.
Figure 3:
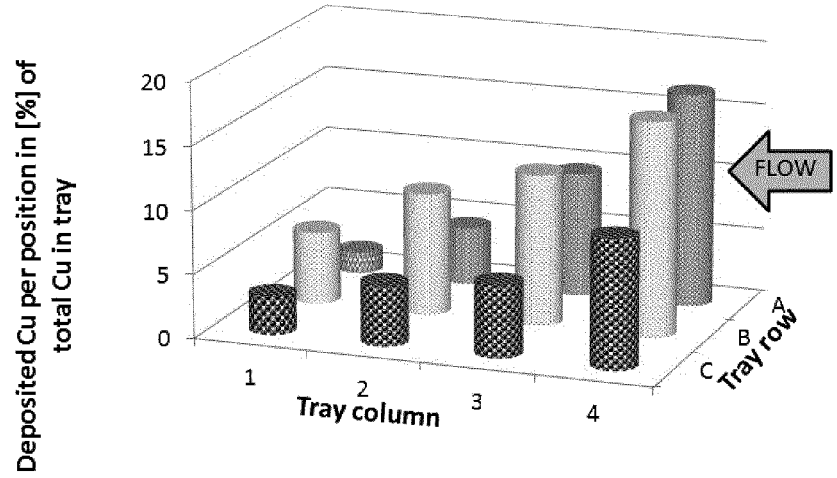
Figure 5:
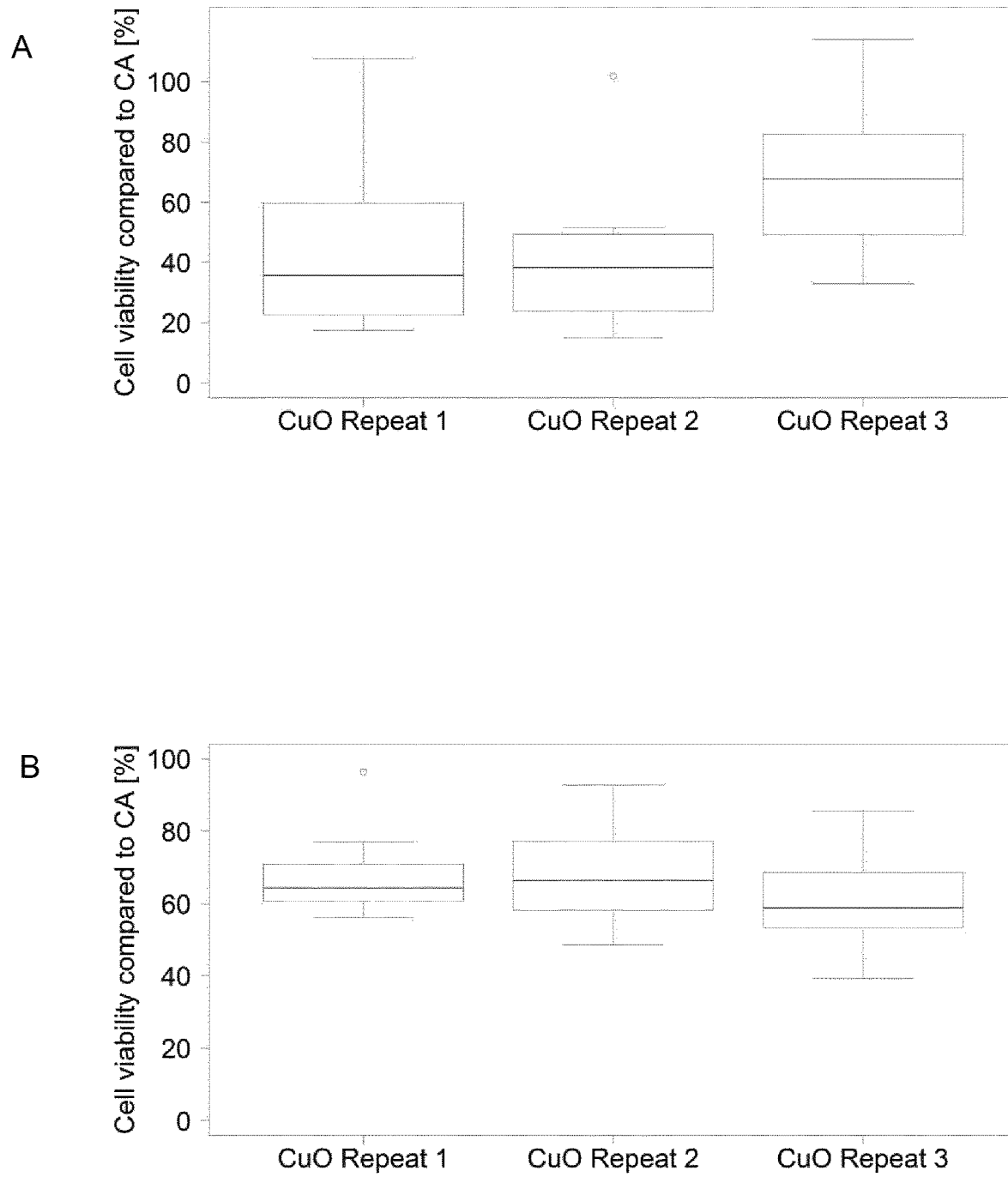
FIG. 5 shows Cell viability (as % compared to clean air, CA) of pIL8-luc (top panel) and NFκB-luc (bottom panel) A549 cells after 1 hour exposure to CuO nanoaerosol at the ALI or CA exposure for 3 independent biological replicates (R1-R3). Boxplots represent analysis of the full tray (A), columns 3 and 4 (B), and individual positions of row 'B' (C). In A and B, each boxplot represents the distribution of the viability data for the 12 versus 6 cell culture inserts in the tray per replicate. In C, each boxplot represents the distribution of the viability data for the 3 independent repeat experiments per position (positions B1 to B4 of tray); *p<0.05; **p≤0.01; 0: outliers.
Figure 5:
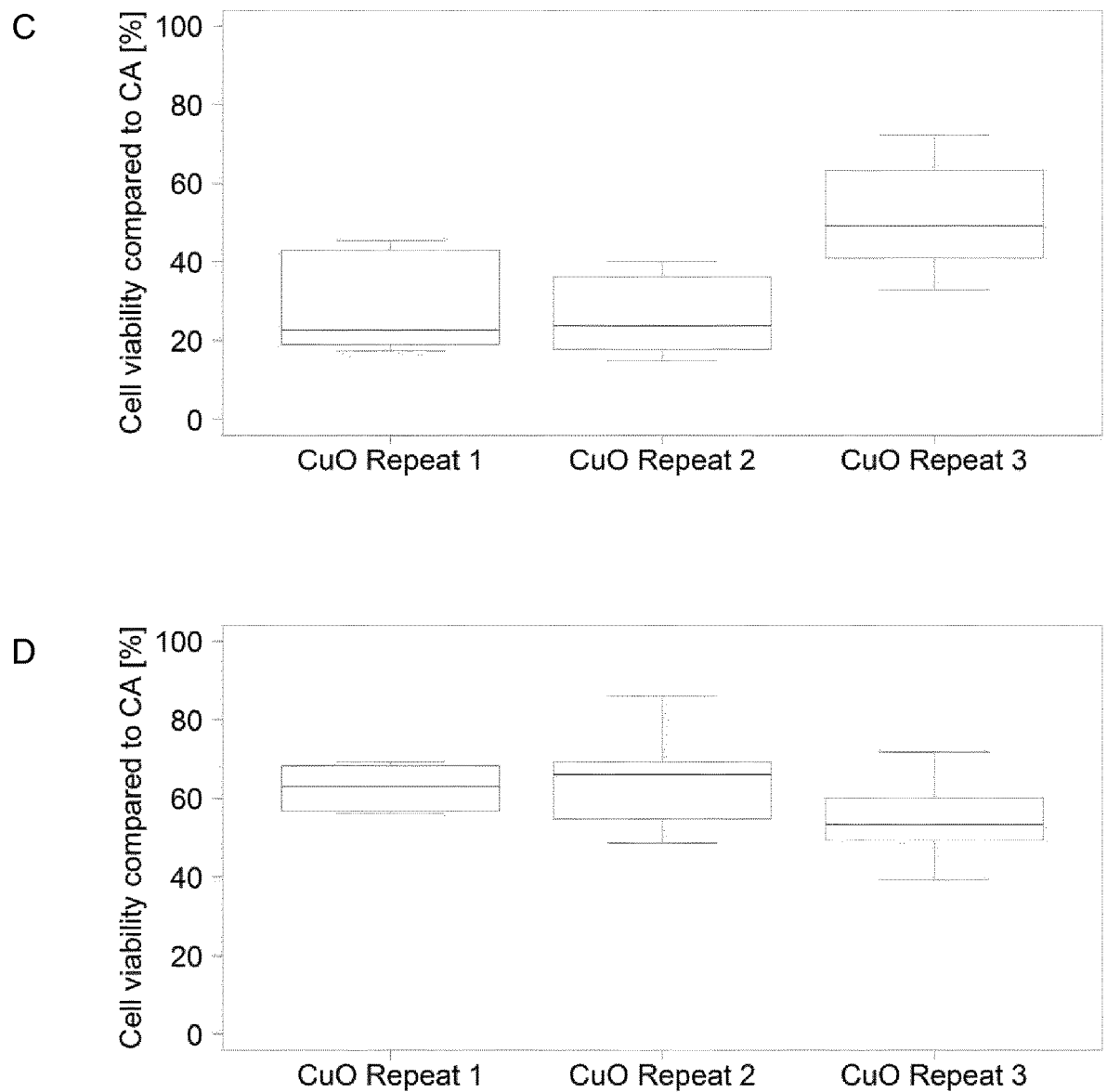
Figure 5:
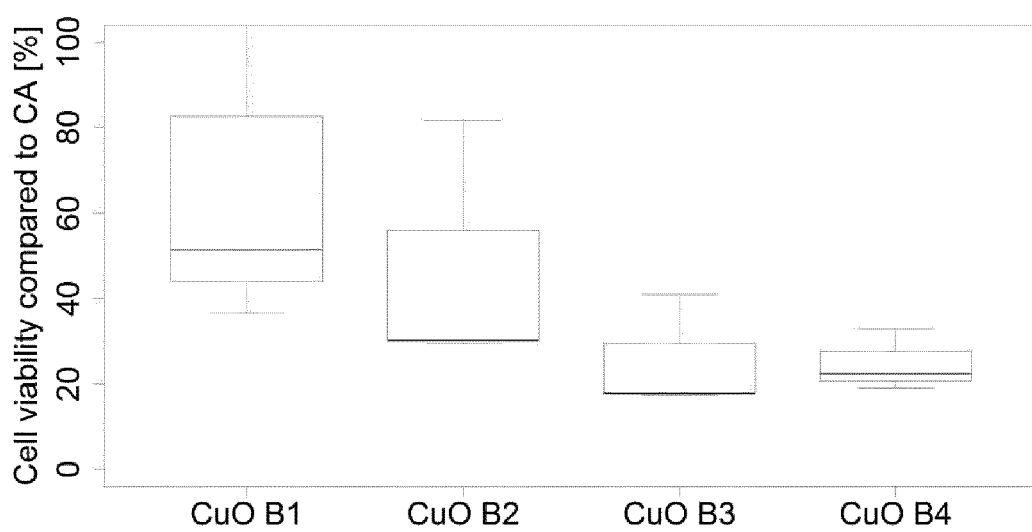
Figure 5:
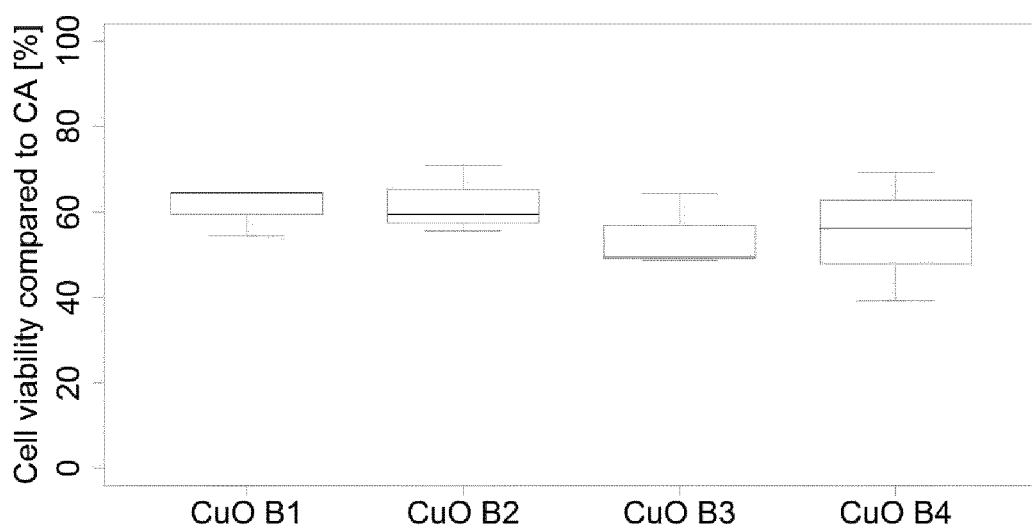

Cell viability of the incubator controls was not significantly different (p=0.52 and p=0.47 for full- and half-tray analysis, respectively) compared to clean air exposure, as expected (data not shown). FIG. 5A shows the cell viability percentages after 1 hour exposure of pIL8-luc cells at the ALI to CuO-NPs versus clean air for 3 independent biological replicates. Each boxplot represents the distribution of the viability data for 12 cell culture inserts in the tray per replicate. It was consistently observed that CuO—NP exposure significantly (p<0.01) reduced cell viability compared to clean air exposure when the 3 repeats were analysed together. For the separate repeats, a maximum of ~85% reduction in cell viability was observed. The same decrease in cell viability was observed after exposure to 12 ppm NO2 as positive control (p<0.01) (data not shown). FIG. 3 shows a higher CuO deposition in columns 3 and 4 and a preferential air flow in row 'B'. The half-tray analysis (FIG. 5B) showed a lower variability in cell viability (p<0.01) under CuO—NP exposure for the three replicates in comparison to the full-tray analysis. In FIG. 5C, each boxplot represents the distribution of the viability data for 3 independent replicates per position in row B. In all B positions reduced cell viability was observed compared to clean air exposure, which was significant at position B2 (p=0.04) and highest at positions B3 (p=0.02) and B4 (p=0.01).

The same CellTiter-Blue® assay and analysis approach was applied for NFκB-luc A549 cells. Cell viability of the incubator controls was not significantly different (p=0.83 and p=0.90 for full- and half-tray analysis, respectively) compared to clean air exposure, again as expected. FIG. 5D shows that CuO—NP exposure significantly (p<0.01) reduced cell viability compared to clean air exposure with a maximum of ~50% reduction of cell viability. This was also observed after $NO_2$ exposure (p<0.01) with a maximum of ~90% reduction in cell viability (data not shown). Evaluation of columns 3 and 4 resulted in smaller variability of the data (p<0.01) in each boxplot compared to full-tray analysis (FIG. 5E). In FIG. 5F, all B positions showed significantly reduced cell viability compared to clean air exposure.

Example 3: Pro-Inflammatory Response to Nanoaerosol Exposure

In this example we describe the pro-inflammatory monitoring upon nanoaerosol exposure in the flatbed air-liquid interface exposure module according to an embodiment of the invention. The present flatbed air-liquid interface exposure module may be used for monitoring pro-inflammatory and other biological responses based on the use of stable reporter cell readouts, two well-characterized stable cells lines addressing relevant pro-inflammatory responses, i.e. NFκB activation and IL-8 promoter induction, were tested.

Figure 6:
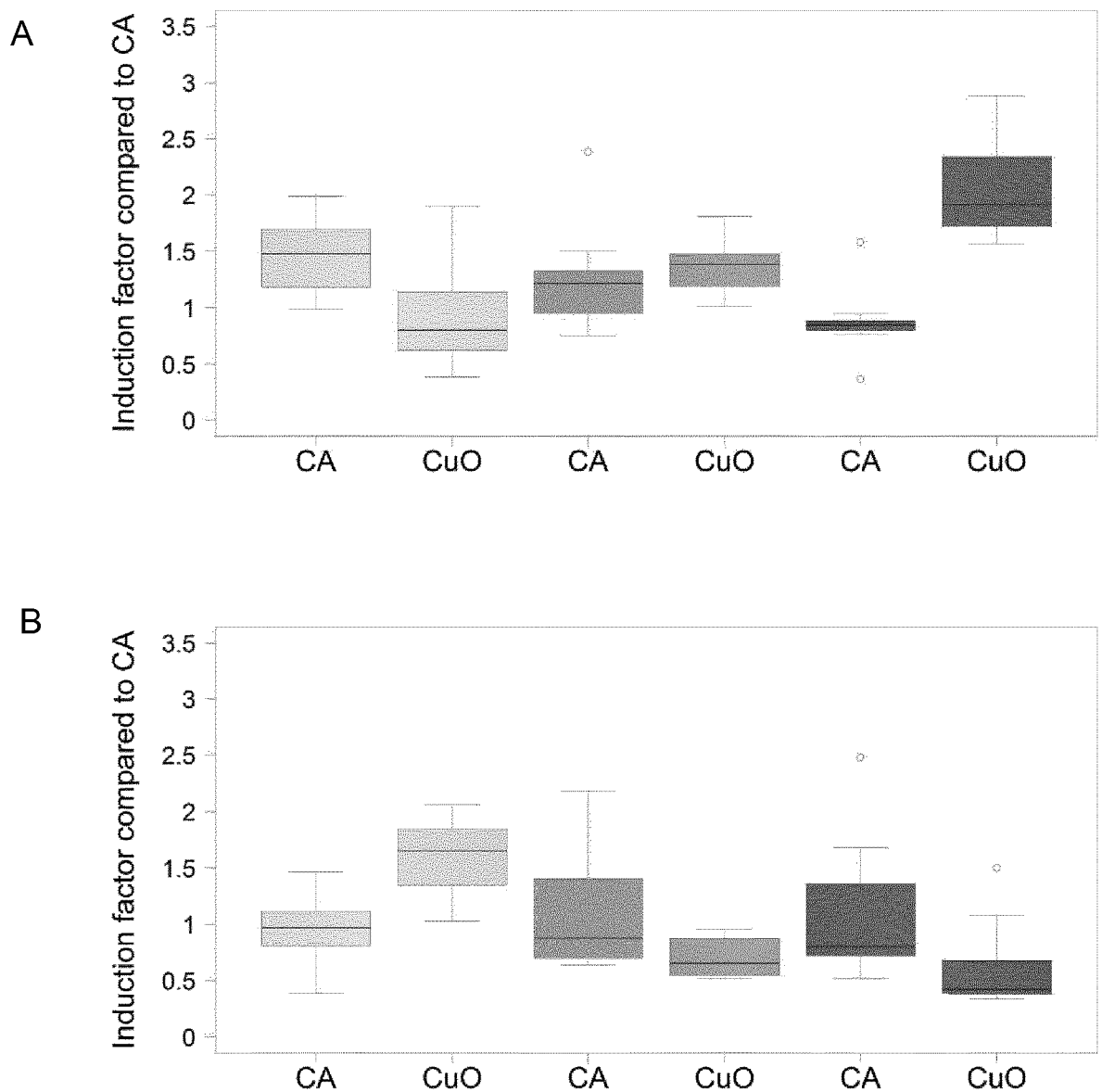
FIG. 6 shows IL-8 promoter activity of pIL8-luc A549 cells (top panel) and NFκB activity of NFκB-luc A549 cells (bottom panel) after 1 hour exposure to CuO nanoaerosol compared to clean air (CA) exposure for 3 independent biological experiments (light (repeat 1), medium (repeat 2), and dark gray (repeat 3)) for analysis of the full tray (A), and columns 3 and 4 (B). Normalization of promoter activity for % cell viability was performed in (C) for analysis of the full tray. 0: outlier.
Figure 6:
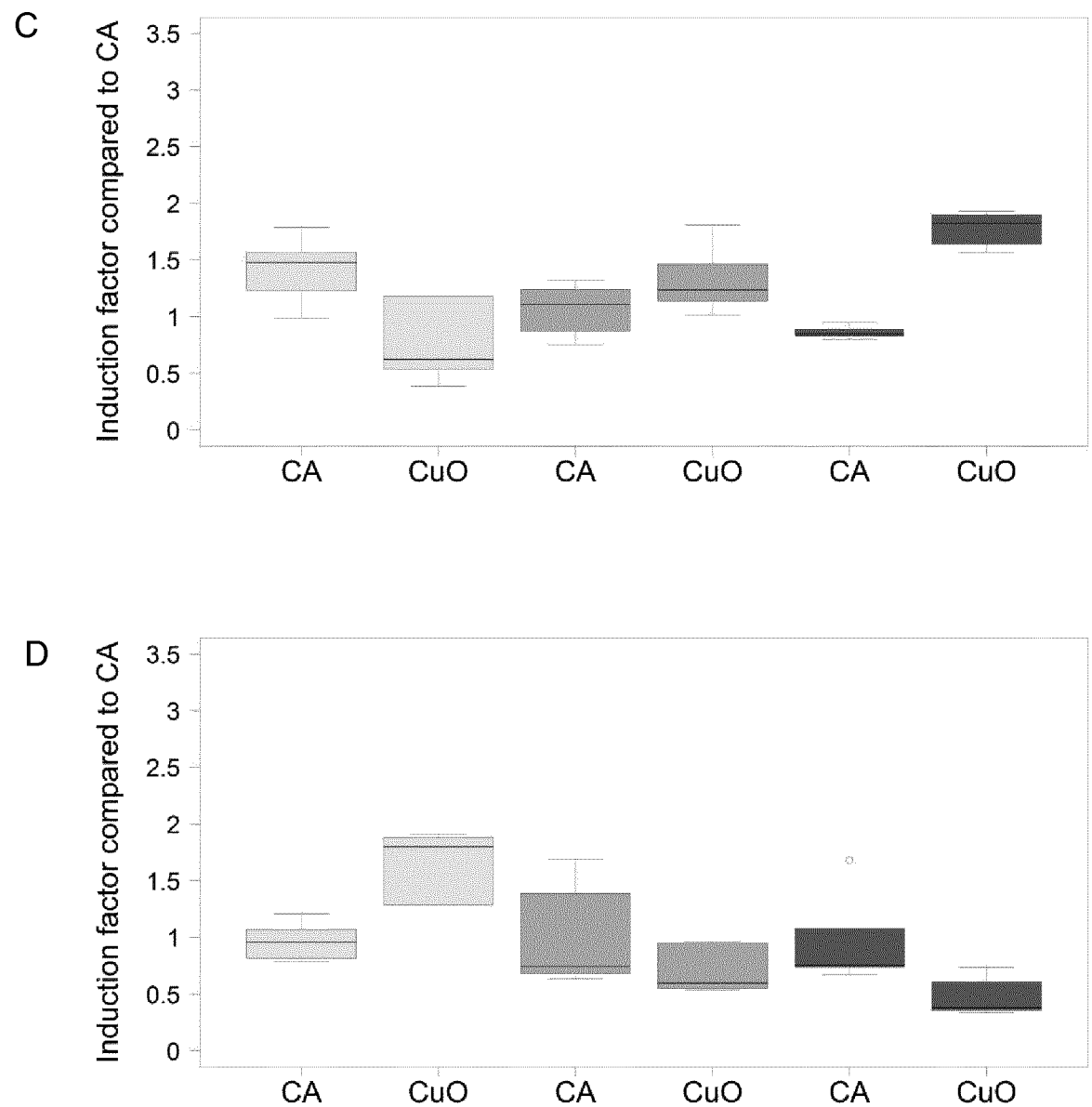
Figure 6:
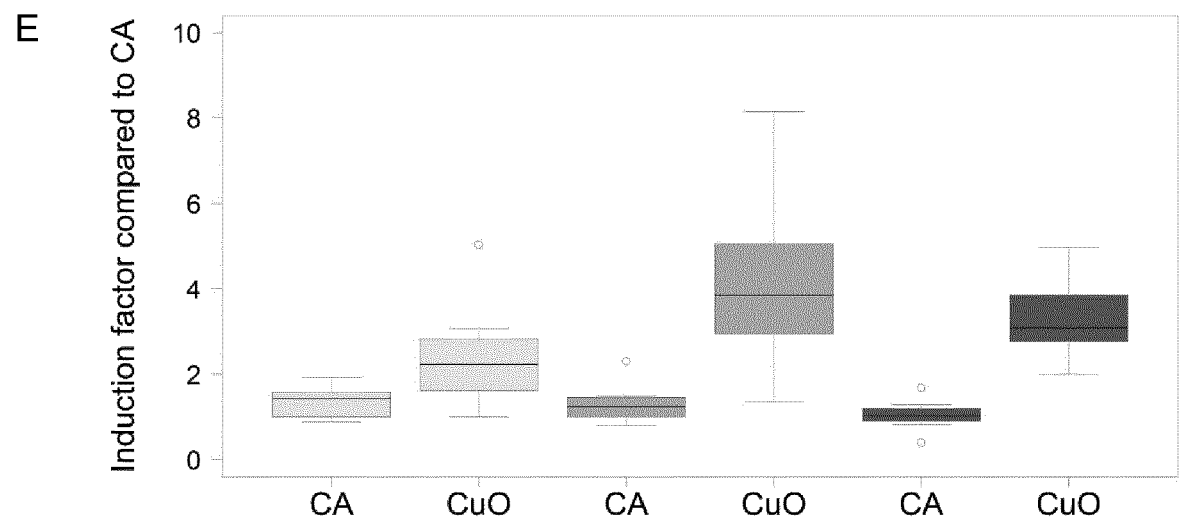
Figure 6:
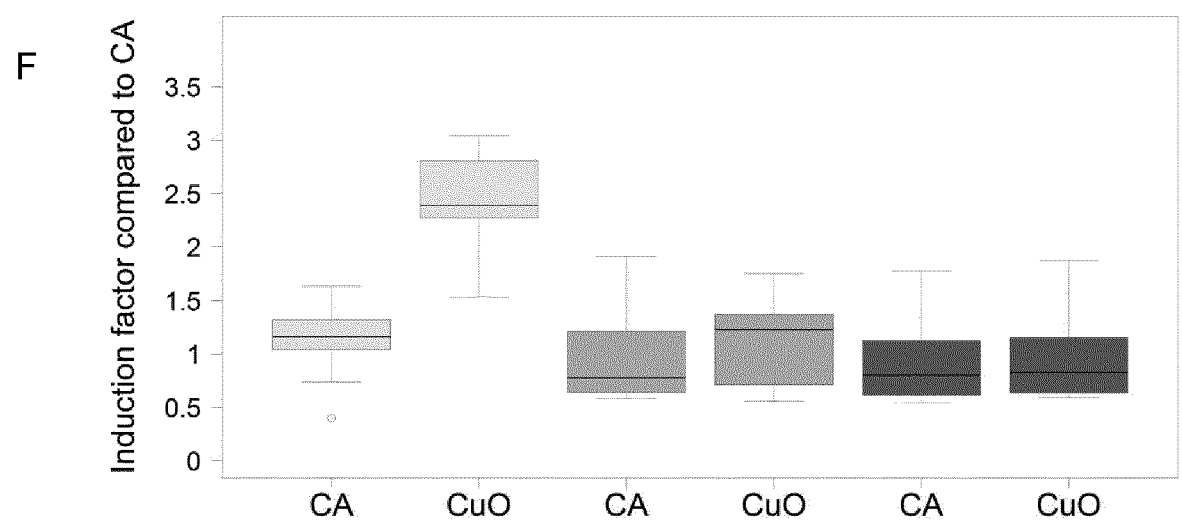

Effects of CuO nanoaerosol exposure on gene promoter activation of the pro-inflammatory cytokine IL-8 were analyzed using the stably transfected p-luc A549 reporter cells. The same analysis approach was applied as for the CellTiter-Blue® assay, i.e. analysis of the full tray, analysis of only column 3 and 4, and only row 'B'. IL-8 promoter activity of the incubator controls was not significantly different (p=0.39 and p=0.55 for full- and half-tray analysis, respectively) compared to clean air exposure, as expected (data not shown). FIG. 6A shows induction of IL-8 promoter activity after 1 hour exposure to clean air versus CuO-NPs for 3 independent biological replicates. Each boxplot represents the distribution of the promoter activity data for 12 cell culture inserts in the tray per replicate. IL8 promoter activity was decreased after CuO-NPs exposure for replicate 1, but an increase was observed for replicates 2 and 3 with a maximum induction factor ~2.9. The overall change in IL-8 promoter activity after CuO-NPs exposure was statistically significantly (p=0.04) different from clean air exposure. As a positive assay control TNF-α (250 ng/ml) was tested in parallel and was observed to induce IL-8 promoter compared to incubator controls with a factor >50 (data not shown). Evaluation of columns 3 and 4 (i.e. 6 technical replicates) resulted in a smaller variability of the data (p=0.21) compared to full-tray analysis (FIG. 6B). No change in IL-8 promoter activity was observed for all B positions (data not shown).

Assuming that cells that are still viable after 20 hours post-exposure incubation contribute most to IL-8 promoter induction after 2.5 hours post-exposure incubation, we normalized the data of IL-8 promoter activity for % cell viability. FIG. 6C shows a significantly (p<0.01) increased IL8 promoter activity after CuO—NP exposure compared to clean air for all 3 replicates.

The same LUC assay and analysis approach was applied for NFκB-luc A549 cells which allows evaluating effects on induction of NFκB response elements. NFκB activity of the incubator controls was not significantly different (p=0.44 and p=0.08 for full- and half-tray analysis, respectively) compared to clean air exposure, as expected. FIG. 6D shows NFκB activity after 1 hour exposure to clean air versus CuO—NP for 3 independent biological replicates. NFκB activity increased after CuO—NP exposure compared to clean air exposure for replicate 1, but a decrease was observed for replicates 2 and 3. The overall change in NFκB activity after CuO—NP exposure was not significantly (p=0.44) different from clean air exposure. The positive control TNF-α (25 ng/ml)) induced NFκB compared to clean air with a factor >3 (data not shown). Evaluation of columns 3 and 4 resulted in a smaller variability of the data in each boxplot compared to full-tray analysis (p=0.77) (FIG. 6E). No change in NFκB activity was observed for all B positions (data not shown). Also here, NFκB activity assessed after 2.5 hours post-exposure was normalized for % cell viability (determined after 20 hours post-exposure incubation). FIG. 6F shows an increased NFκB activity, in particular for replicate 1. Overall, a significantly increased ($p<0.01$) NFκB activity after CuO-NPs exposure compared to clean air for all 3 replicates was found.

Example 12

Figure 7:
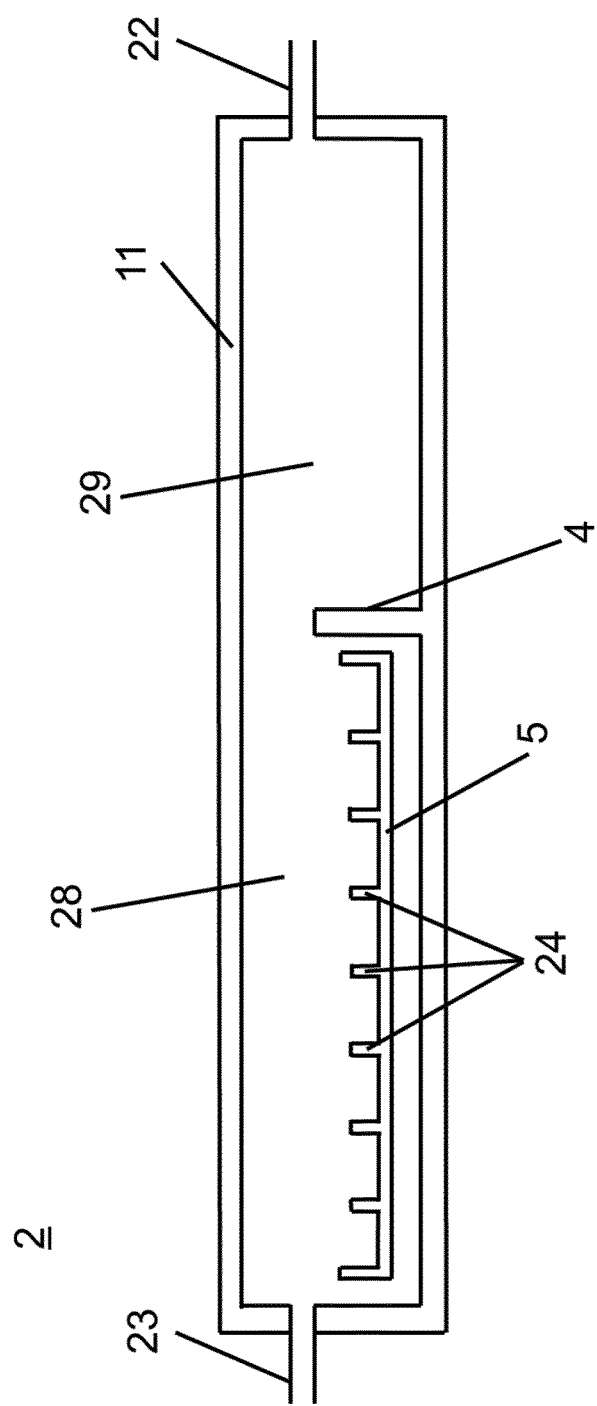
FIG. 7 shows a further detail of a flatbed air-liquid interface exposure module (2) according to an embodiment of the invention (2), comprising an exposure section (28) comprising a metal plate (5) with stubs (24) and a moisturizing section (29).
Figure 8:
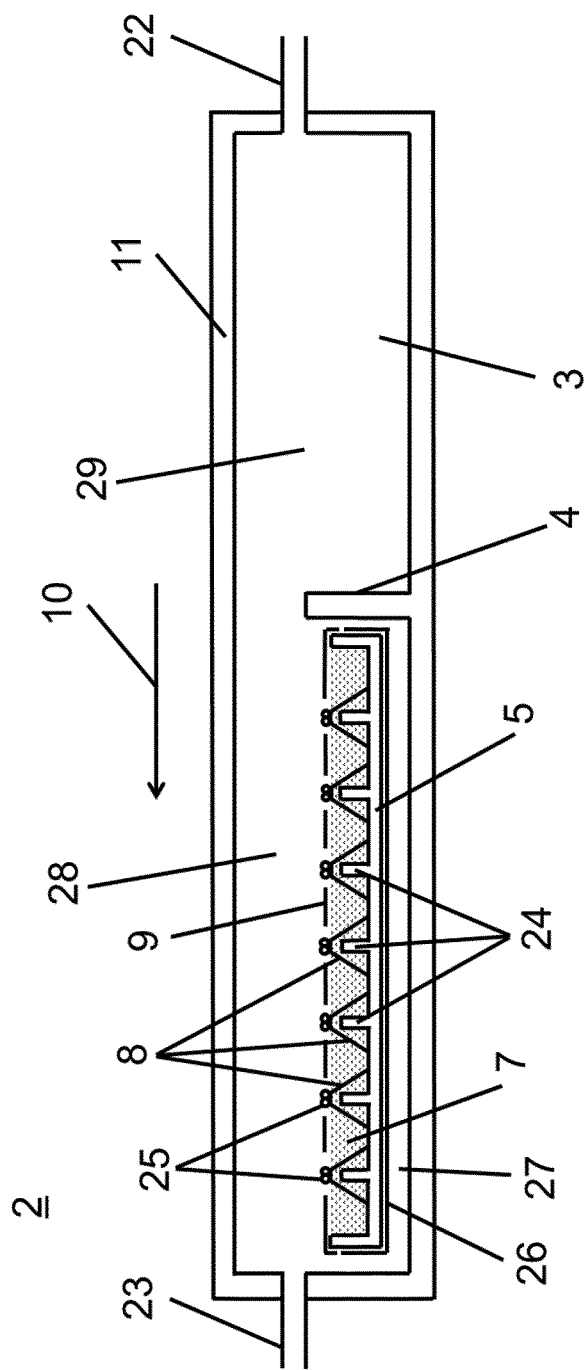
FIG. 8 shows a flatbed air-liquid interface exposure module (2) according to a particular embodiment of the invention including inverted wells (8) and an insulating housing comprising an insulating lid (9).

In a further example, reference is made to FIGS. 7 and 8. FIG. 7 shows a number of non-disposable components of an flatbed air-liquid interface exposure module (2) as provided herein. FIG. 8 shows the same flatbed air-liquid interface exposure module including a number of disposable components.

In particular, FIG. 7 shows flatbed air-liquid interface exposure module (2) comprising an exposure section (28) and a moisturizing section (29) which are encased by a casing (11) and which are separated by a bridge (4). An inlet (22) is provided for allowing an aerosol comprising charged nanoparticles to enter the moisturizing section (29). Also, an outlet (23) is provided for venting aerosol depleted of nanoparticles from the exposure section (28). The exposure section (28) comprises a stainless steel plate (5) which in turn comprises a plurality of stubs (24) which protrude from the stainless steel plate into the exposure section (28).

In FIG. 8, the moisturizing section (29) is provided with water, thereby forming a water bath (3) for moisturizing an aerosol comprising charged nanoparticles. The exposure section is also provided with water (27). The stainless steel plate (5) is shielded from the water (27) in the exposure section by means of a polystyrene tub (26). Inverted wells (8) are positioned over the stubs (24) of the metal plate (5). The inverted wells (8) support cells (25). The metal plate is provided with cell culture medium (7) for providing nutrients and water to the cells (25). The cell culture medium (7) is present between the inverted wells (25), and between the metal plate (5) and the inverted wells (25). A polystyrene lid (9) comprising a plurality of holes is further provided. The holes are aligned with the cells such that the polystyrene lid (9) can effectively help directing charged nanoparticles to the cells (25) on the inverted wells (8).

The invention claimed is:

1. A flatbed air-liquid interface exposure module, the flatbed air-liquid interface exposure module comprising a moisturizing section, an exposure section, and an aerosol duct;
the exposure section comprising a means for ensuring an electric field comprising a metal plate, which comprises a plurality of discrete stubs which protrude from the metal plate into the exposure section, and further comprising an inverted well cell culture set-up comprising inverted wells for supporting cells at an air-liquid interface, the inverted wells being positioned over the plurality of stubs of the metal plate;
the aerosol duct being configured for sequentially guiding an aerosol flow comprising charged nanoparticles through the moisturizing section and the exposure section, and for guiding the humidified aerosol flow horizontally over the plurality of inverted wells.

2. The flatbed air-liquid interface exposure module according to claim 1, wherein the exposure section further comprises an upper metal component, wherein the means for generating an electric field is formed by the metal plate and the upper metal component, and wherein the discrete stubs protrude from the metal plate towards the upper metal component.

3. The flatbed air-liquid interface exposure module according to claim 1, wherein the moisturizing section comprising a water-bath.

4. The flatbed air-liquid interface exposure module according to claim 1, wherein each inverted well comprising a porous membrane for supporting a plurality of the cells at the air-liquid interface.

5. The flatbed air-liquid interface exposure module according to claim 1, wherein the exposure section further comprises an insulating housing comprising at least an insulating lid, the insulating lid comprising a plurality of holes, the insulating lid being positioned above the inverted well cell culture set-up, and the holes being aligned with the inverted wells.

6. The flatbed air-liquid interface exposure module according to claim 5 wherein the insulating lid is removable.

7. The flatbed air-liquid interface exposure module according to claim 5, wherein the insulating housing also encompasses said metal plate.

8. The flatbed air-liquid interface exposure module according to claim 1, wherein the exposure section further comprises a temperature controller.

9. The flatbed air-liquid interface exposure module according to claim 8 wherein the temperature controller comprises one or more Peltier elements and a heat sink, the Peltier elements being thermally coupled to the heat sink.

10. The flatbed air-liquid interface exposure module according to claim 1 further comprising a gravimetric sensor, a temperature sensor, and a humidity sensor.

11. The flatbed air-liquid interface exposure module according to claim 1 further comprising a bridge between the moisturizing section and the exposure section.

12. An air-liquid interface exposure system comprising a nanoparticle charging device, a fluidic system, a high voltage source and a flatbed air-liquid interface exposure module according to claim 1, wherein:
the nanoparticle charging device is configured for charging nanoparticles in an aerosol comprising uncharged nanoparticles, thereby obtaining an aerosol comprising charged nanoparticles;
the fluidic system is configured for directing the aerosol comprising charged nanoparticles through the flatbed air-liquid interface exposure module; and
the high voltage source is connected to the metal plate to ensure an electric field.

13. An air-liquid interface exposure system according to claim 12, which further comprises one or more of one or more control units for controlling temperature and relative humidity within the flatbed air-liquid interface exposure module, a scanning mobility particle sizer (SMPS) and/or an exhaust which is connected to a pump connected to a mass flow controller (MFC).

14. A method for exposing a plurality of cells in vitro to nanoparticles comprised in an aerosol, comprising the following consecutive steps:
a. providing the cells in an flatbed air-liquid interface exposure module according to claim 1,
b. allowing the aerosol comprising charged nanoparticles to pass through the flatbed air-liquid interface exposure module; and
c. generating an electric field in the exposure section of said flatbed air-liquid interface exposure module, so as to direct the charged nanoparticles aerosol to the cells.

15. The method according to claim 14 wherein the plurality of cells comprises cells selected from the list consisting of airway epithelial cells and alveolar epithelial cells.

\* \* \* \* \*